US007655936B2

(12) United States Patent
Sawayama et al.

(10) Patent No.: US 7,655,936 B2
(45) Date of Patent: Feb. 2, 2010

(54) OPTICAL SENSOR AND IMAGE FORMING APPARATUS THAT PROCESSES SPECULAR REFLECTION LIGHT

(75) Inventors: Noboru Sawayama, Tokyo (JP); Kayoko Ikegami, Saitama (JP); Katsuo Hatase, Saga (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 12/044,565

(22) Filed: Mar. 7, 2008

(65) Prior Publication Data
US 2008/0170220 A1 Jul. 17, 2008

Related U.S. Application Data

(62) Division of application No. 10/819,318, filed on Apr. 7, 2004, now abandoned.

(30) Foreign Application Priority Data

Apr. 7, 2003 (JP) .............................. 2003-102745
Apr. 7, 2003 (JP) .............................. 2003-102766
Sep. 19, 2003 (JP) .............................. 2003-327264

(51) Int. Cl.
*G01N 21/86* (2006.01)
*G03G 15/00* (2006.01)

(52) U.S. Cl. ..................... 250/559.4; 399/49
(58) Field of Classification Search ........... 250/216, 250/559.16, 559.4; 399/49; 356/600, 237.1, 356/446, 448
See application file for complete search history.

(56) References Cited

U.S. PATENT DOCUMENTS

| | | | |
|---|---|---|---|
| 3,591,291 A | 7/1971 | Greer et al. | |
| 5,304,812 A | 4/1994 | Tani et al. | |
| 6,642,505 B1 | 11/2003 | Nakano et al. | |
| 7,221,805 B1 * | 5/2007 | Bachelder | .................... 382/255 |
| 2003/0007752 A1 | 1/2003 | Oka et al. | |
| 2004/0141764 A1 | 7/2004 | Runkowske et al. | |

FOREIGN PATENT DOCUMENTS

| | | |
|---|---|---|
| JP | 64-35466 | 2/1989 |
| JP | 03-110450 | 5/1991 |
| JP | 3-67458 | 7/1991 |
| JP | 5-5786 | 1/1993 |
| JP | 05-322758 | 12/1993 |
| JP | 9-129858 | 5/1997 |
| JP | 9-504875 | 5/1997 |
| JP | 9-321597 | 12/1997 |
| JP | 11-094694 | 4/1999 |
| JP | 11-211660 | 8/1999 |
| JP | 2000039746 | 2/2000 |

(Continued)

*Primary Examiner*—Thanh X Luu
(74) *Attorney, Agent, or Firm*—Oblon, Spivak, McClelland, Maier & Neustadt, L.L.P.

(57) ABSTRACT

An optical sensor includes at least one light emitting unit that emits a light, a first light receiving unit that receives specular reflection light from an illumination object when the light is incident on the illumination object with an incidence angle and specularly reflected with a reflection angle, and a second light receiving unit that receives diffuse reflection light from the illumination object when the incident light is diffusely reflected at the illumination object. The sum of the incident angle and the reflection angle is 25 degrees or less.

7 Claims, 20 Drawing Sheets

FOREIGN PATENT DOCUMENTS

| | | |
|---|---|---|
| JP | 2000-250304 | 9/2000 |
| JP | 2000-322990 | 11/2000 |
| JP | 2001-334572 | 12/2001 |
| JP | 2002-55174 | 2/2002 |
| JP | 2002-207404 | 7/2002 |
| JP | 2004-147027 | 5/2004 |
| WO | WO 95/13529 | 5/1995 |

* cited by examiner

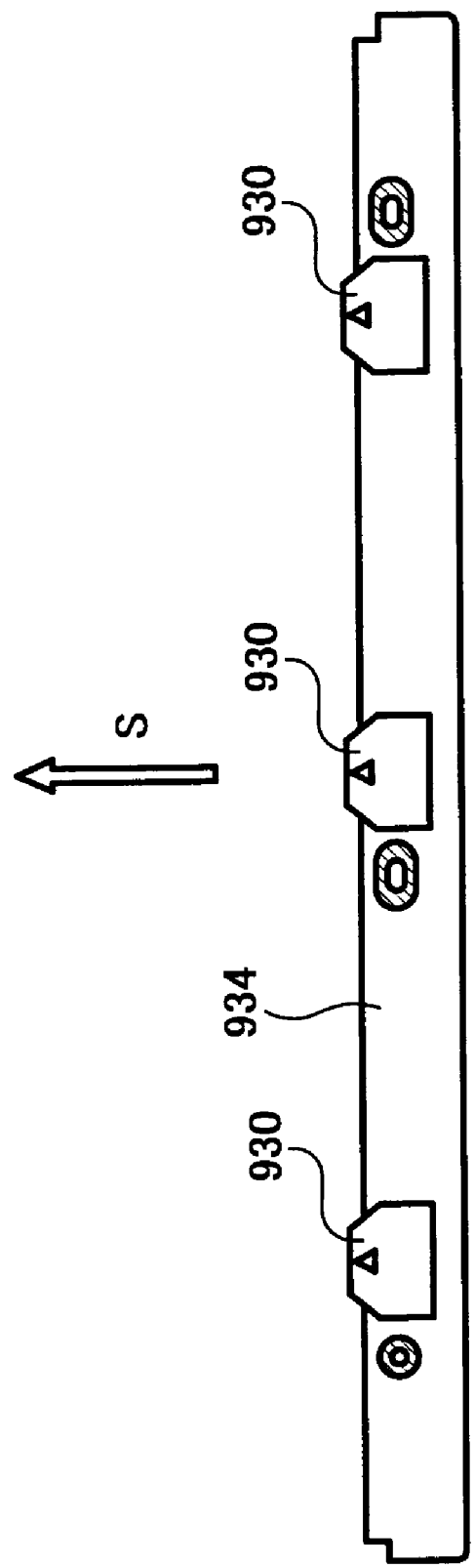

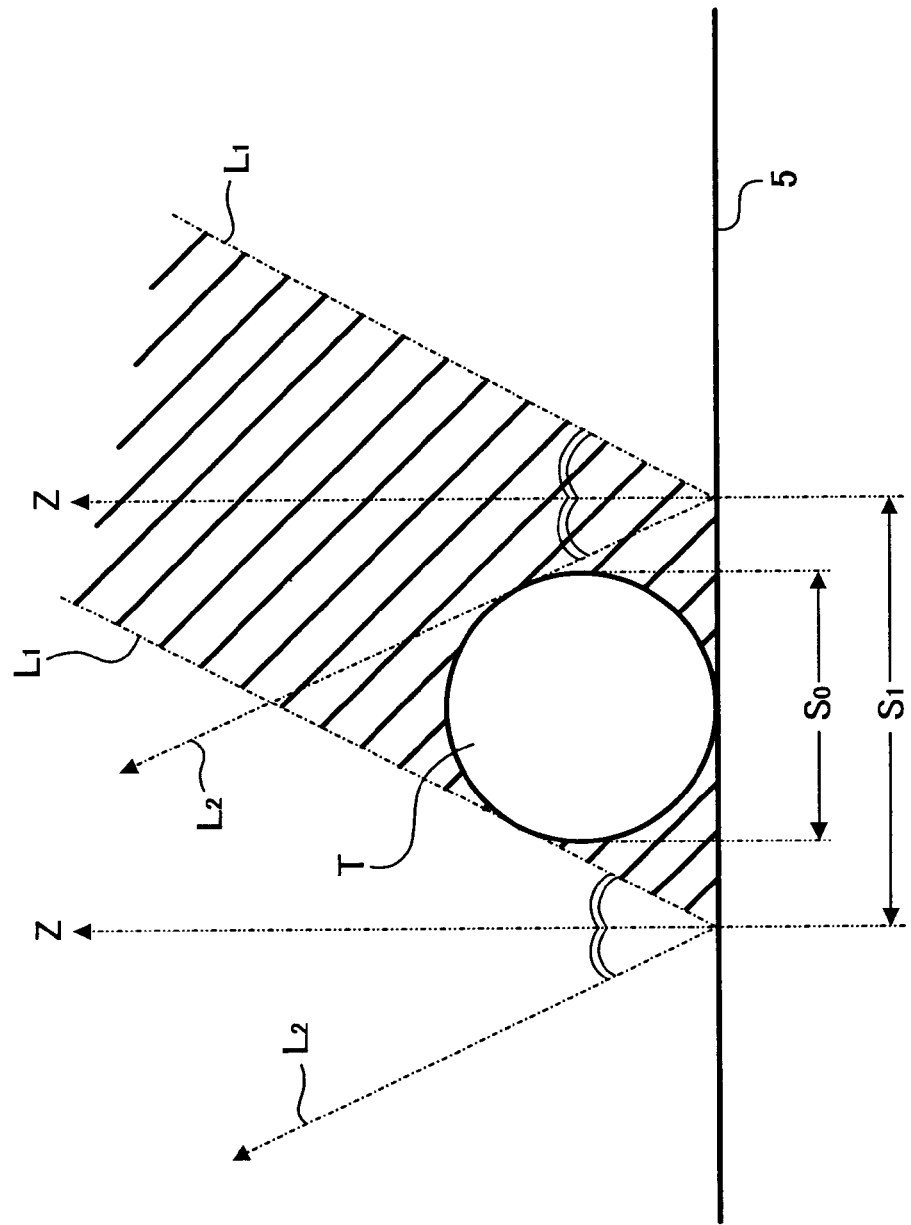

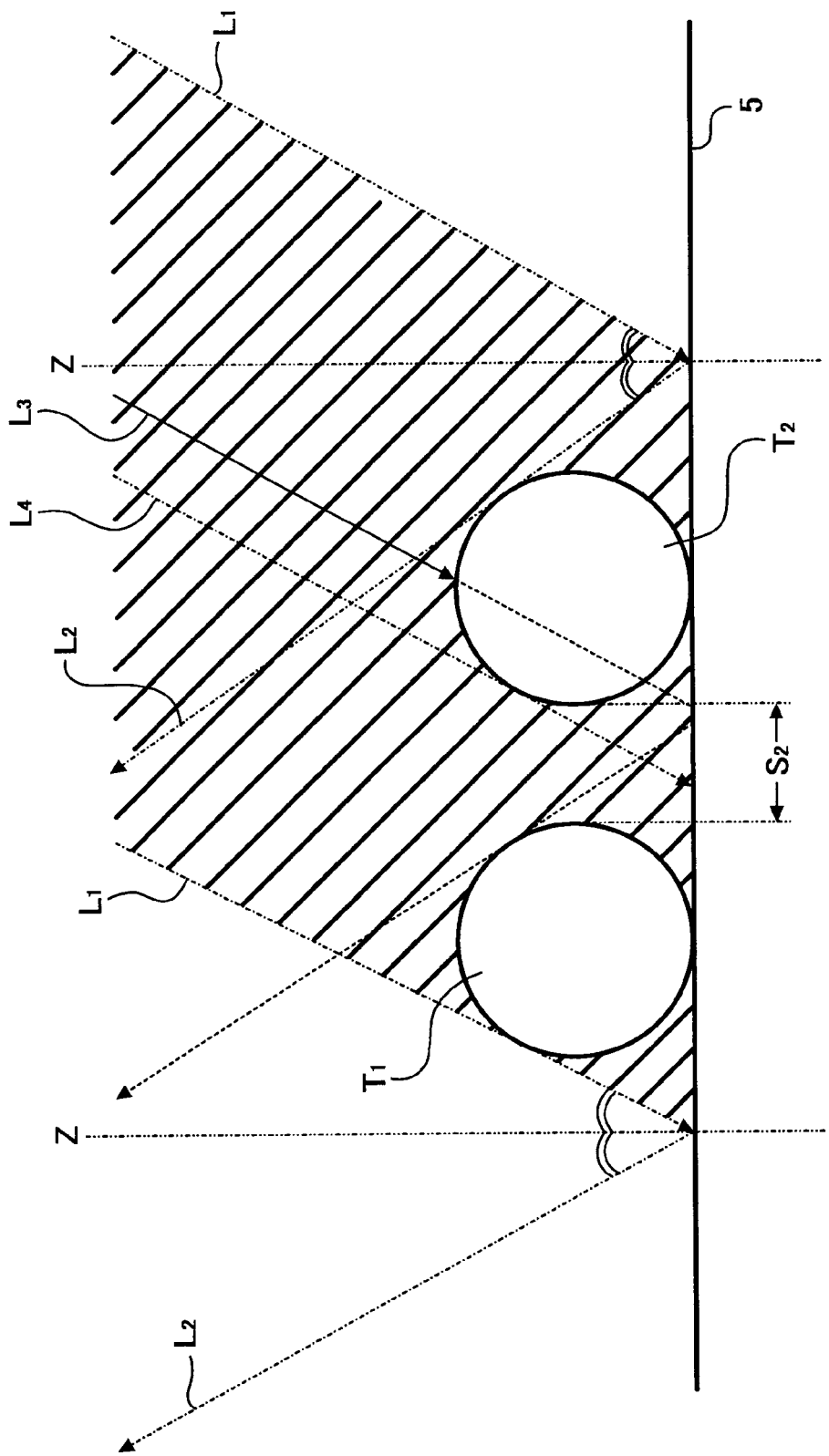

ically reflected by the surface of the photosensitive drum, and specular reflection light is received by a light-receiving element in accordance with the reflectance of the surface of the photosensitive drum. Conversely, when toner adheres to the surface of the photosensitive drum, the incident light is absorbed by the toner or reflected diffusely by the toner. Hence, in cases where incident light is blocked by toner before reaching the surface of the photosensitive drum, or specular reflection light from the surface of the photosensitive drum is blocked by toner before reaching the light-receiving element, no specular reflection light is received by the light-receiving element. Thus the amount of light received by the light-receiving element decreases as the amount of toner which adheres to the surface of the photosensitive drum increases. Accordingly, the toner adhesion amount on the surface of the photosensitive drum can be detected on the basis of the amount of light received by the light-receiving element.

OPTICAL SENSOR AND IMAGE FORMING APPARATUS THAT PROCESSES SPECULAR REFLECTION LIGHT

CROSS-REFERENCE TO RELATED APPLICATIONS

This is a divisional of U.S. application Ser. No. 10/819,318 filed Apr. 7, 2004 now abandoned. The present document incorporates by reference the entire contents of Japanese priority documents, 2003-102745 filed in Japan on Apr. 7, 2003, 2003-102766 filed in Japan on Apr. 7, 2003 and 2003-327264 filed in Japan on Sep. 19, 2003.

BACKGROUND OF THE INVENTION

1) Field of the Invention

The present invention relates to an optical sensor that receives the specular reflection light of incident light irradiated onto an illumination object, and an image formation apparatus that employs the optical sensor.

2) Description of the Related Art

An image formation apparatus such as that disclosed in Japanese Unexamined Patent Application Publication S64-35455, for example, is known as an image formation apparatus using an optical sensor. In this type of image formation apparatus, a density-detecting toner patch (reference pattern) is created on the surface of an image carrier such as a photosensitive body in order to obtain a stable image density, and the density of the patch is detected by an optical sensor. In this image formation apparatus, image density control is performed on the basis of the detection results of the optical sensor to adjust the development potential by modifying the fabrication light intensity for latent image formation, charging bias, developing bias, and so on, or to adjust the target toner density value inside the developing machine when a two-component developing system is used. The optical sensor uses the reference pattern as a detection object, and is therefore known as a P (pattern) sensor. A reflection optical sensor comprising light emitting unit and light receiving unit is typically used as the optical sensor.

A type of reflection optical sensor is known which detects specular reflection light generated when the light irradiated onto an illumination object is specularly reflected. This type of reflection optical sensor is disclosed in Patent Document 1 and so on. Taking a case in which toner density (the toner adhesion amount) on a photosensitive drum is detected, the detection principle employed when a reflection optical sensor which detects specular reflection light is used as a P sensor is as follows.

When no toner adheres to the surface of the photosensitive drum (illumination object), the incident light is specularly reflected by the surface of the photosensitive drum, and specular reflection light is received by a light-receiving element in accordance with the reflectance of the surface of the photosensitive drum. Conversely, when toner adheres to the surface of the photosensitive drum, the incident light is absorbed by the toner or reflected diffusely by the toner. Hence, in cases where incident light is blocked by toner before reaching the surface of the photosensitive drum, or specular reflection light from the surface of the photosensitive drum is blocked by toner before reaching the light-receiving element, no specular reflection light is received by the light-receiving element. Thus the amount of light received by the light-receiving element decreases as the amount of toner which adheres to the surface of the photosensitive drum increases. Accordingly, the toner adhesion amount on the surface of the photosensitive drum can be detected on the basis of the amount of light received by the light-receiving element.

An optical sensor using lead-type elements, for example, is also known as a conventional reflection optical sensor. In an optical sensor using lead-type elements, a light-emitting element and a light-receiving element are fixed in a resin case formed with an indentation which matches the elements. The light-emitting element and light-receiving element are connected to a substrate by lead wires, and thus light emitting signals or light receiving signals are exchanged with the main body of the apparatus. In an optical sensor using lead-type elements, the elements are fixed inside a resin case, and hence the positioning accuracy of the light-emitting element and light-receiving element is dependent on the manufacturing precision of the resin case. Since the resin case is a molded product, irregularities in the manufacturing precision are virtually nonexistent. Hence by creating a resin case which matches the optical system, a reflection optical sensor with a high degree of element positioning accuracy can be obtained.

An optical sensor using surface mounted elements, in which the elements are placed directly onto a substrate without the use of leads, is also known. By using these surface mounted elements, reductions in cost and improvements in productivity can be achieved in comparison with conventional lead-type elements, and moreover, the entire optical sensor can be reduced in size.

However, the following problems are encountered in conventional optical sensors and image formation apparatuses such as those described above.

FIG. 23A and FIG. 23B are schematics for illustrating states that toner is transferred to the surface of a photosensitive drum 5 serving as an illumination object. When the surface of the photosensitive drum 5 is irradiated with incident light $L_1$ from a light-emitting element, not shown in the drawing, of a P sensor, and the incident light $L_1$ is not obstructed by toner T, the incident light $L_1$ is specularly reflected by the photosensitive drum surface, and the resultant specular reflection light $L_2$ is received by a light-receiving element not shown in the drawing. However, the incident light in the region of the drawing indicated by diagonal lines is obstructed by the toner T and cannot reach the light-receiving element. When detecting specular reflection light, the optical path of the incident light must be inclined in relation to the normal direction Z of the photosensitive drum surface. Hence a surface area $S_1$ of the part of the photosensitive drum surface which does not contribute to the specular reflection light that is received by the light-receiving element is larger than the surface area of orthogonal projection of the toner T in relation to the photosensitive drum surface, or in other words a surface area $S_0$ of the part of the photosensitive drum surface that is actually occupied by toner. More specifically, the proportion of the surface area $S_1$ of the part of the photosensitive drum surface which does not contribute to the specular reflection light that is received by the light-receiving element in relation to the surface area $S_0$ of the part of the photosensitive drum surface that is actually occupied by toner (hereinafter, "the shadow factor") increases. Hence, as shown in FIG. 23B, when a toner particle $T_2$ approaches another toner particle $T_1$, the specular reflection light of a space $S_2$ between the toner particles is not received by the light-receiving element even though no toner exists in the space $S_2$. As a result, at the stage when toner is transferred to the photosensitive drum at intervals of approximately the space $S_2$, it becomes difficult to detect the adherence of more toner using a P sensor. Hence in regions where a large amount of toner is transferred to the photosensitive drum surface, the sensitivity of the P sensor which detects specular reflection light decreases, and thus it becomes difficult to detect the toner adhesion amount.

FIG. 24 is a graph for illustrating a relationship between an amount of black toner transferred to the surface of the photosensitive drum and the output voltage of the P sensor that detects specular reflection light. FIG. 25 is a graph for illustrating a relationship between an amount of color toner transferred to the surface of the photosensitive drum and the output voltage of the P sensor that detects specular reflection light. As can be seen from these graphs, in the case of both black toner and color toner, variation in the output voltage of the P sensor in relation to increases in the amount of transferred toner is sufficiently large up to an adhesion amount of approximately 0.3 mg/cm$^2$, and hence the toner adhesion amount can be detected. However, when the adhesion amount exceeds this level, there is substantially no change in the output voltage of the P sensor, and hence the toner adhesion amount cannot be detected. Note that in the case of color toner, as shown in FIG. 25, the output voltage of the P sensor switches from monotonous decreasing to monotonous increasing on reaching approximately 0.4 mg/cm$^2$. This is a phenomenon which occurs due to a property according to which black toner absorbs light, but color toner diffusely reflects light. In other words, according to this phenomenon, in the case of color toner, diffuse reflection light that is diffusely reflected by the color toner is received by the light-receiving element as well as specular reflection light, and the amount of diffuse reflection light received by the light-receiving element increases as the toner adhesion amount increases.

Particularly in recent years, the miniaturization of toner particle diameter has progressed and the roundness of toner has improved, and hence limits on the detection of toner adhesion amounts by a P sensor which detects specular reflection light have become substantially narrower. To explain this using the graphs shown in FIG. 24 and FIG. 25, the point at which variation in the output voltage of the P sensor in relation to the toner adhesion amount substantially ceases is currently shifting to a lower toner adhesion amount.

More specifically, in the case of a fine particle toner having a weight average particle diameter of 8 micrometers or less, the surface area of a recording paper surface that is covered when a single toner particle is spread over the recording paper by the heat and pressure generated upon adhesion is small. Accordingly, in order to obtain a uniform image density, more toner must be used as the particle diameter of the toner decreases. Hence, when detecting the toner adhesion amount on the surface of an image carrier so as to obtain a desired image density, regions in which the toner adhesion amount is large in accordance with the small particle diameter of the toner must be detected with good sensitivity. In other words, since the toner adhesion amount detection range of the P sensor shifts toward the high adhesion amount side as the particle diameter of the toner decreases, limits on the detection of the toner adhesion amount by the P sensor become substantially narrower. Moreover, as shown by the graphs in FIG. 24 and FIG. 25, the toner adhesion amount is typically expressed as a toner weight per surface area unit, and the toner weight is proportionate to the toner volume. In this case, if the toner radius is assumed to be R, then the toner volume decreases in proportion to $1/R^3$ as the toner diameter is reduced, and hence the toner weight also decreases in proportion to $1/R^3$. As a result, the point at which variation in the output voltage of the P sensor in relation to the toner adhesion amount substantially ceases shifts to a lower toner adhesion amount, and hence limits on the detection of the toner adhesion amount by the P sensor become even narrower.

In the case of toner having a high degree of roundness, in which the average roundness is 0.93 or more, the aforementioned shadow factor tends to increase. As a result, the sensitivity of the P sensor which detects specular reflection light in relation to regions on the photosensitive drum surface having a large toner adhesion amount decreases, making it difficult to detect the adhesion amount in such regions.

An optical sensor used to detect an amount of toner transferred to a photosensitive drum was described above, but any optical sensor which receives specular reflection light to detect the amount of an illumination object which does not specularly reflect light existing on an object which specularly reflects light also possess similar problems regarding the narrowness of the detectable range.

Further, the positioning accuracy of a surface mounted light-emitting element or light-receiving element is dependent on the positioning accuracy when the surface mounted element is surface mounted on a substrate. However, this positioning accuracy is limited, and a degree of positioning accuracy as high as that obtained with a lead-type element, where element positioning is performed using a resin case, cannot be achieved. Hence in a conventional optical sensor using surface mounted elements, irregularities occur in the positioning accuracy of the light-emitting element or light-receiving element even in identical products. As a result, a uniform light receiving sensitivity cannot be obtained when an illumination object is irradiated with light from the light-emitting element. In other words, irregularities occur in the detection characteristic of a sensor even when the product is identical.

SUMMARY OF THE INVENTION

It is an object of the present invention to solve at least the problems in the conventional technology.

The optical sensor according to one aspect of the present invention includes at least one light emitting unit that emits a light; a first light receiving unit that receives specular reflection light from an illumination object when the light is incident on the illumination object with an incidence angle and specularly reflected with a reflection angle; and a second light receiving unit that receives diffuse reflection light from the illumination object when the incident light is diffusely reflected at the illumination object. The sum of the incident angle and the reflection angle is 25 degrees or less.

The optical sensor according to another aspect of the present invention includes at least one light emitting unit that emits a light; a first light receiving unit that receives specular reflection light from an illumination object when the light is incident on the illumination object with an incidence angle and specularly reflected with a reflection angle; and a second light receiving unit that receives diffuse reflection light from the illumination object when the incident light is diffusely reflected at the illumination object. A light condensing member is provided on at least one of incident light path along which the light from the light emitting unit travels to the illumination object, a specular reflection light path along which the specular reflection light travels to the first light receiving unit, and diffuse reflection light path along which the diffuse reflection light travels to the second light receiving unit.

The optical sensor according to still another aspect of the present invention includes at least one light emitting unit that emits a light; a first light receiving unit that receives specular reflection light from an illumination object when the light is incident on the illumination object with an incidence angle and specularly reflected with a reflection angle; and a second light receiving unit that receives diffuse reflection light from the illumination object when the incident light is diffusely reflected at the illumination object. The at least one of the at least one light emitting unit and the first light receiving unit is formed by a surface mounted optical means in which an optical element is surface mounted on a substrate.

The optical sensor according to still another aspect of the present invention includes at least one light emitting unit that emits a light; a first light receiving unit that receives specular reflection light from an illumination object when the light is incident on the illumination object with an incidence angle and specularly reflected with a reflection angle; and a second light receiving unit that receives diffuse reflection light from the illumination object when the incident light is diffusely reflected at the illumination object. The second light receiving unit is disposed outside of a virtual plane including incident light path along which the light from the light emitting unit travels to the illumination object and the specular reflection light path along which the specular reflection light travels to the first light receiving unit.

The image formation apparatus according to still another aspect of the present invention includes an image carrier having a surface that specularly reflects a light; a toner image forming unit that forms a toner image on the image carrier; an optical sensor that detects an amount of toner transfer when the toner image forming unit transfers toner to the image carrier to form the toner image; and an image density control unit that controls an image density based on a result of detection by the optical sensor. The optical sensor includes at least one light emitting unit that emits a light; a first light receiving unit that receives specular reflection light from an illumination object when the light is incident on the illumination object with an incidence angle and specularly reflected with a reflection angle; and a second light receiving unit that receives diffuse reflection light from the illumination object when the incident light is diffusely reflected at the illumination object. The sum of the incident angle and the reflection angle is 25 degrees or less.

The image formation apparatus according to still another aspect of the present invention includes an image carrier having a surface that specularly reflects a light; a toner image forming unit that forms a toner image on the image carrier; an optical sensor that detects an amount of toner transfer when the toner image forming unit transfers toner to the image carrier to form the toner image; and an image density control unit that controls an image density based on a result of detection by the optical sensor. The optical sensor includes at least one light emitting unit that emits a light; a first light receiving unit that receives specular reflection light from an illumination object when the light is incident on the illumination object with an incidence angle and specularly reflected with a reflection angle; and a second light receiving unit that receives diffuse reflection light from the illumination object when the incident light is diffusely reflected at the illumination object. A light condensing member is provided on at least one of incident light path along which the light from the light emitting unit travels to the illumination object, a specular reflection light path along which the specular reflection light travels to the first light receiving unit, and diffuse reflection light path along which the diffuse reflection light travels to the second light receiving unit.

The image formation apparatus according to still another aspect of the present invention includes an image carrier having a surface that specularly reflects a light; a toner image forming unit that forms a toner image on the image carrier; an optical sensor that detects an amount of toner transfer when the toner image forming unit transfers toner to the image carrier to form the toner image; and an image density control unit that controls an image density based on a result of detection by the optical sensor. The optical sensor includes at least one light emitting unit that emits a light; a first light receiving unit that receives specular reflection light from an illumination object when the light is incident on the illumination object with an incidence angle and specularly reflected with a reflection angle; and a second light receiving unit that receives diffuse reflection light from the illumination object when the incident light is diffusely reflected at the illumination object. The at least one of the at least one light emitting unit and the first light receiving unit is formed by a surface mounted optical means in which an optical element is surface mounted on a substrate.

The image formation apparatus according to still another aspect of the present invention includes an image carrier having a surface that specularly reflects a light; a toner image forming unit that forms a toner image on the image carrier; an optical sensor that detects an amount of toner transfer when the toner image forming unit transfers toner to the image carrier to form the toner image; and an image density control unit that controls an image density based on a result of detection by the optical sensor. The optical sensor includes at least one light emitting unit that emits a light; a first light receiving unit that receives specular reflection light from an illumination object when the light is incident on the illumination object with an incidence angle and specularly reflected with a reflection angle; and a second light receiving unit that receives diffuse reflection light from the illumination object when the incident light is diffusely reflected at the illumination object. The second light receiving unit is disposed outside of a virtual plane including incident light path along which the light from the light emitting unit travels to the illumination object and the specular reflection light path along which the specular reflection light travels to the first light receiving unit.

The optical sensor according to still another aspect of the present invention includes at least one light emitting unit that emits a light; and a light receiving unit that receives specular reflection light from an illumination object when the light is incident on the illumination object with an incidence angle and specularly reflected with a reflection angle. The sum of the incident angle and the reflection angle is 25 degrees or less.

The optical sensor according to still another aspect of the present invention includes at least one light emitting unit that emits a light; and a light receiving unit that receives specular reflection light from an illumination object when the light is incident on the illumination object with an incidence angle and specularly reflected with a reflection angle. A light condensing member is provided on at least one of incident light path along which the light from the light emitting unit travels to the illumination object, a specular reflection light path along which the specular reflection light travels to the light receiving unit, and diffuse reflection light path along which the diffuse reflection light travels to the second light receiving unit.

The optical sensor according to still another aspect of the present invention includes at least one light emitting unit that emits a light; and a light receiving unit that receives specular reflection light from an illumination object when the light is incident on the illumination object with an incidence angle and specularly reflected with a reflection angle. The at least one of the at least one light emitting unit and the first light receiving unit is formed by a surface mounted optical means in which an optical element is surface mounted on a substrate.

The image formation apparatus according to still another aspect of the present invention includes an image carrier having a surface that specularly reflects a light; a toner image forming unit that forms a toner image on the image carrier; an optical sensor that detects an amount of toner transfer when the toner image forming unit transfers toner to the image carrier to form the toner image; and an image density control unit that controls an image density based on a result of detection by the optical sensor. The optical sensor includes at least one light emitting unit that emits a light; and a light receiving unit that receives specular reflection light from an illumination object when the light is incident on the illumination object with an incidence angle and specularly reflected with a reflection angle. The sum of the incident angle and the reflection angle is 25 degrees or less.

The image formation apparatus according to still another aspect of the present invention includes an image carrier having a surface that specularly reflects a light; a toner image forming unit that forms a toner image on the image carrier; an optical sensor that detects an amount of toner transfer when the toner image forming unit transfers toner to the image carrier to form the toner image; and an image density control unit that controls an image density based on a result of detection by the optical sensor. The optical sensor includes at least one light emitting unit that emits a light; and a light receiving unit that receives specular reflection light from an illumination object when the light is incident on the illumination object with an incidence angle and specularly reflected with a reflection angle. A light condensing member is provided on at least one of incident light path along which the light from the light emitting unit travels to the illumination object, a specular reflection light path along which the specular reflection light travels to the light receiving unit, and diffuse reflection light path along which the diffuse reflection light travels to the second light receiving unit.

The image formation apparatus according to still another aspect of the present invention includes an image carrier having a surface that specularly reflects a light; a toner image forming unit that forms a toner image on the image carrier; an optical sensor that detects an amount of toner transfer when the toner image forming unit transfers toner to the image carrier to form the toner image; and an image density control unit that controls an image density based on a result of detection by the optical sensor. The optical sensor includes at least one light emitting unit that emits a light; and a light receiving unit that receives specular reflection light from an illumination object when the light is incident on the illumination object with an incidence angle and specularly reflected with a reflection angle. The at least one of the at least one light emitting unit and the first light receiving unit is formed by a surface mounted optical means in which an optical element is surface mounted on a substrate.

The optical sensor according to still another aspect of the present invention includes at least one light emitting unit that emits a light; and at least one light receiving unit that receives specular reflection light from an illumination object when the light is incident on the illumination object with an incidence angle and specularly reflected with a reflection angle. At least one of the at least one light emitting unit and the at least one light receiving unit is surface mounted onto a circuit board. A hole forming member that forms a light transmitting hole is provided on a light path between at least one of the at least one light emitting unit and the at least one light receiving unit and the illumination object, a cross section of the light transmitting hole is smaller a cross section of the light path.

The image formation apparatus according to still another aspect of the present invention includes an image carrier having a surface that specularly reflects a light; a toner image forming unit that forms a toner image on the image carrier; an optical sensor that detects an amount of toner transfer when the toner image forming unit transfers toner to the image carrier to form the toner image; and an image density control unit that controls an image density based on a result of detection by the optical sensor. The optical sensor includes at least one light emitting unit that emits a light; and at least one light receiving unit that receives specular reflection light from an illumination object when the light is incident on the illumination object with an incidence angle and specularly reflected with a reflection angle. At least one of the at least one light emitting unit and the at least one light receiving unit is surface mounted onto a circuit board. A hole forming member that forms a light transmitting hole is provided on a light path between at least one of the at least one light emitting unit and the at least one light receiving unit and the illumination object, a cross section of the light transmitting hole is smaller a cross section of the light path.

The other objects, features, and advantages of the present invention are specifically set forth in or will become apparent from the following detailed description of the invention when read in conjunction with the accompanying drawings.

BRIEF DESCRIPTION OF THE DRAWINGS

FIG. 22 is a schematic for illustrating an example of assembly of the optical sensor;

FIG. 23A and FIG. 23B are schematics for illustrating states that toner is transferred to a surface of a photosensitive drum;

DETAILED DESCRIPTION

Exemplary embodiments of an optical sensor and an image forming apparatus according to the present invention are explained in detail with reference to the accompanying drawings. Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

Figure 2:
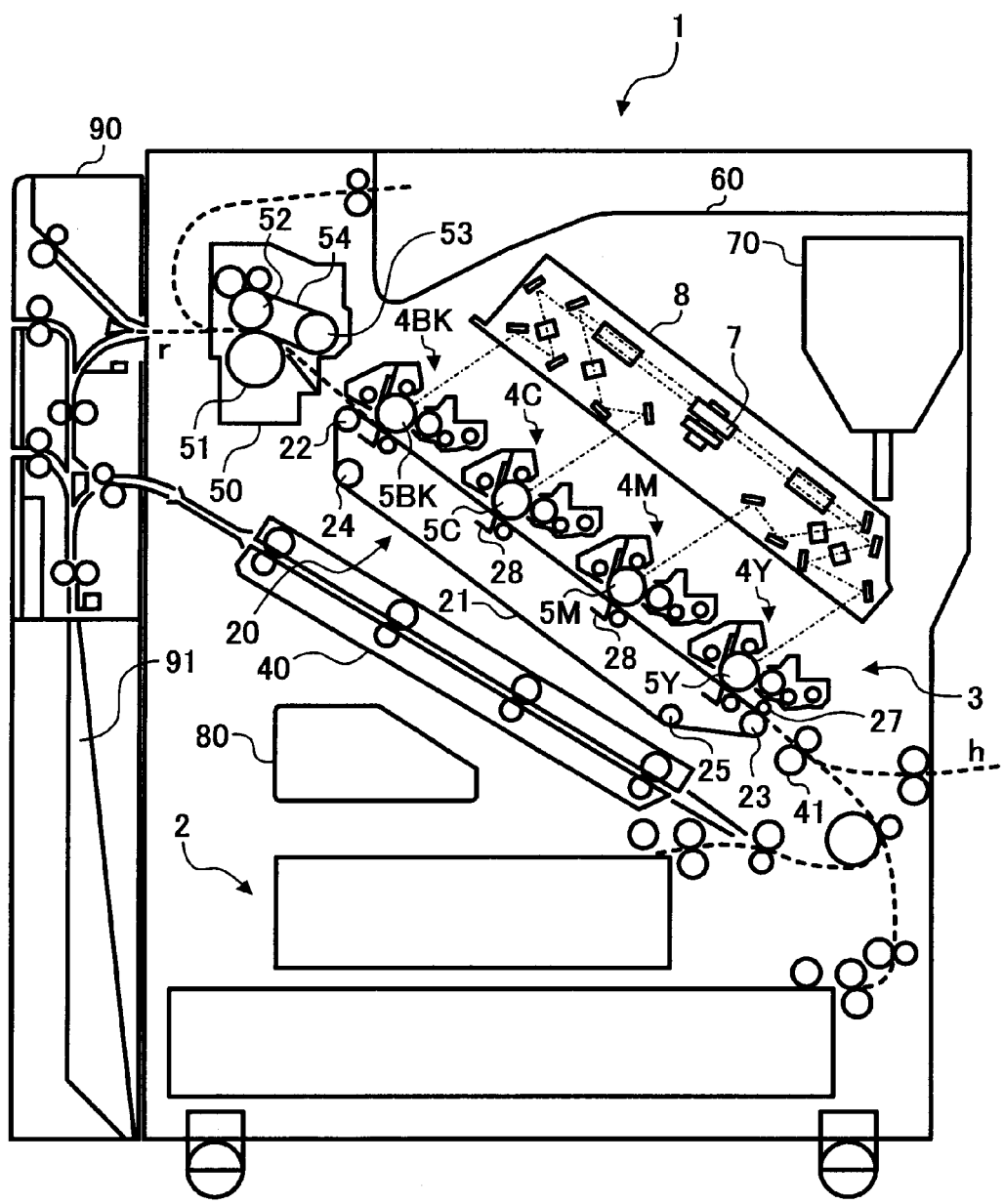
FIG. 2 is a cross section of the printer.

FIG. 2 is a cross section of a printer according to a first embodiment of the present invention. A paper feeding portion 2 is provided in the lower portion of the main body of the apparatus, and an image-forming portion 3 is disposed above. A paper delivery tray 60 is formed on the upper face of the apparatus. The broken line in the drawing indicates a conveyance path for recording paper serving as a recording material. The recording paper is supplied from the paper feeding portion 2, whereupon an image formed in the image-forming portion 3 is transferred onto the surface of the recording paper. The image is fixed by a fixing apparatus 50, and then the recording paper is discharged to the paper delivery tray 60. Note that paper may be fed manually from the side face of the apparatus, as shown by the reference symbol h in the drawing. Further, a two-surface apparatus 90 is attached to the side face of the apparatus main body. When images are to be formed on both surfaces of the recording paper, an image is formed and fixed on one surface, whereupon the recording paper is conveyed along a broken line r in the drawing. The front and rear of the recording paper are then switched in the two-surface apparatus 90, whereupon the recording paper is fed through a reconveyance portion 40 so that an image can be formed on the other surface.

A transfer conveyor belt apparatus 20 disposed at an incline such that the paper feeding side is at the bottom and the paper delivery side is at the top is provided in the image-forming portion 3. Four image-forming units 4Y, 4M, 4C, 4Bk for yellow (Y), magenta (M), cyan (C), and black (Bk) respectively are disposed in series from the bottom side of the transfer conveyor belt apparatus 20 along its upper running surface. The image-forming units 4Y, 4M, 4C, and 4Bk are constituted identically, and hence the magenta image-forming unit 4M will be used as an example hereinafter.

Figure 3:
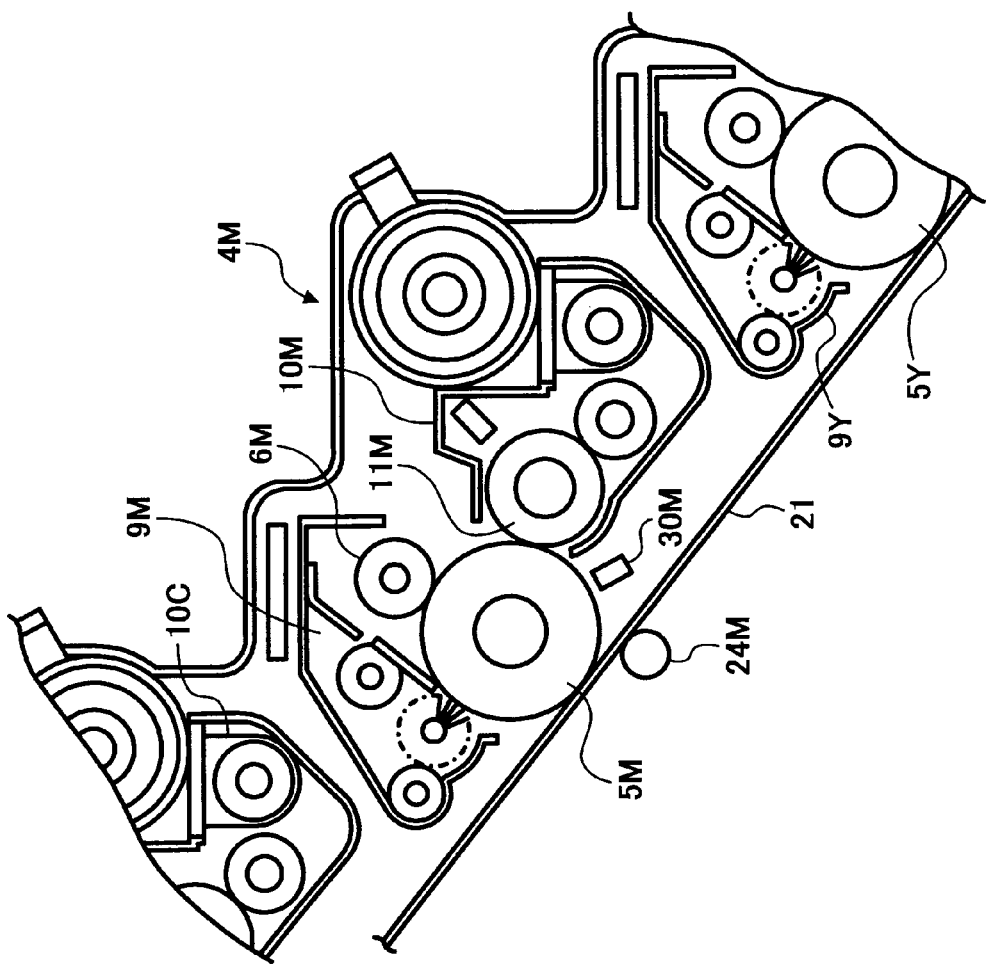
FIG. 3 is an enlarged view of a magenta image-forming unit of the printer.

FIG. 3 is an enlarged view of the magenta image-forming unit 4M of the printer. The image-forming unit 4M comprises a photosensitive drum 5M which serves as an image carrier, and the photosensitive drum 5M is driven to rotate in the clockwise direction of the drawing by driving means not shown in the drawing. A charging roll 6M, a developing apparatus 10M, a cleaning apparatus 9M, a toner adhesion amount detection sensor (hereinafter, "P sensor") 30M, and so on are provided around the photosensitive drum 5M. The developing apparatus 10M provides the photosensitive drum 5M with toner that is held in a developing sleeve 11M serving as a developer holding body. As shown in FIG. 2, laser light from an optical fabrication apparatus 8 serving as latent image forming unit is irradiated onto the photosensitive drum 5M from between the charging roll 6M and developing sleeve 11M. Note that a detailed description of the constitution and operation of the P sensor 30M will be provided below.

An endless belt-form transfer conveyor belt 21 is provided on the transfer conveyor belt apparatus 20. This transfer conveyor belt 21 is stretched over a driving roller 22, a driven roller 23, and tension rollers 24, 25. A transfer brush 28 constituting transfer means contacts each of the photosensitive drums 5M, 5C, 5Y, 5Bk of the color image-forming units 4M, 4C, 4Y, 4Bk in a position opposing each of the photosensitive drums 5M, 5C, 5Y, 5Bk on the inside of the upper running surface of the transfer conveyor belt 21. A transfer bias having an opposite polarity (plus polarity) to the charged polarity of the toner (which is minus polarity in the first embodiment) is applied to the transfer brush 28. A paper adsorbing roller 27 is provided above the driven roller 23 so as to sandwich the transfer conveyor belt 21. The recording paper is discharged over the transfer conveyor belt 21 from between the driven roller 23 and the adsorbing roller 27, and electrostatically conveyed over the transfer conveyor belt 21 in an adsorbed state by the bias voltage that is applied to the adsorbing roller 27. In the first embodiment, the linear process speed is set to 125 mm/sec, and hence the recording paper is conveyed at this speed.

In the first embodiment, the fixing apparatus 50 employs a belt fixing system, and is constituted by wrapping a fixing belt 54 around a fixing roller 52 and a heating roller 53. The fixing roller 52 and a pressurizing roller 51 are pressed against each other to form a fixing nip. A heater not shown in the drawing is installed inside the heating roller 53 and pressurizing roller 51.

In the following description, the color differentiating symbols Y, M, C, and Bk have been omitted where appropriate.

The photosensitive drums 5Y, 5M, 5C, 5Bk in each of the color image-forming units 4Y, 4M, 4C, 4Bk are driven to rotate by a main motor not shown in the drawing. First, the surface of each of the photosensitive drums 5Y, 5M, 5C, 5Bk is neutralized by an AC bias (zero DC component) applied to the charging roller 6, whereby the surface potential reaches approximately −50V in this embodiment. Next, by applying a voltage in which an AC voltage and a DC voltage are superimposed to the charging roller 6, the photosensitive drums 5Y, 5M, 5C, 5Bk are charged uniformly to a substantially equal potential to the DC component of this voltage, whereby the surface potential is charged to approximately −500V to −700V in this embodiment. Note that the target charging potential is determined by a process control portion not shown in the drawing.

The optical fabrication apparatus 8 then forms an electrostatic latent image corresponding to each color on the surface of each of the photosensitive drums 5Y, 5M, 5C, 5Bk charged in this manner. The optical fabrication apparatus 8 drives an LD (laser diode) not shown in the drawing on the basis of image data transmitted from a host machine such as a personal computer, and thus irradiates a polygon mirror 7 with laser light. This laser light is led to the surface of the photosensitive drums 5Y, 5M, 5C, 5Bk through a cylindrical lens or the like. The surface potential of the photosensitive body at the part that is irradiated with laser light reaches approximately −50V, and this part becomes the electrostatic latent image to be developed by toner.

When toner is applied to the electrostatic latent image from the developing apparatus 10, toner images in the respective colors are formed on the surface of the photosensitive drums 5Y, 5M, 5C, 5Bk. In this embodiment, a developing bias (−300V to −500V) in which a DC voltage and an AC voltage are superimposed is applied to the developing sleeve 11. As a result, a developing field causes the minus polarity toner held in the developing sleeve 11 to become transferred to only the surface part (electrostatic latent image part) of the photosensitive drums 5Y, 5M, 5C, 5Bk having a reduced potential as a result of optical fabrication, and not to the surface part (non-electrostatic latent image part) of the photosensitive drums 5Y, 5M, 5C, 5Bk where optical fabrication has not been performed and the potential is not reduced. Thus toner images of each color are formed respectively on the electrostatic latent image part of the photosensitive drums 5Y, 5M, 5C, 5Bk.

Meanwhile, recording paper is fed from the paper feeding portion 2, whereupon the fed recording paper first impinges on a pair of resist rollers 41 provided on the upstream side of the transfer conveyor belt apparatus 20 in the direction of conveyance. The recording paper is then conveyed by the transfer conveyor belt 21 in synchronization with the transfer timing of each color toner image to reach a transfer position opposing the photosensitive drums 5Y, 5M, 5C, 5Bk. A transfer field is formed in this transfer position by the action of the transfer bias that is applied to the transfer brush 28 disposed on the rear face side of the transfer conveyor belt 21. This transfer field causes the color toner images on the photosensitive drums 5Y, 5M, 5C, 5Bk to be transferred successively onto the recording material so as to overlap each other.

Note that in cases where a monochrome image is printed, a toner image is formed using black toner only on the photosensitive drum 5Bk of the black image-forming unit 4Bk, whereupon the recording paper is conveyed by the transfer conveyor belt 21 in synchronization with the transfer timing of this toner image such that only a black toner image is transferred.

Thus the recording paper onto which the color toner images have been transferred is stripped from the transfer conveyor belt 21 at the position of the drive roller 22 and then conveyed to the fixing apparatus 50. When passing through the fixing nip of the fixing apparatus 50, the color toner images are fixed onto the recording paper by heat and pressure. Once fixing is completed, the recording paper is discharged to the paper delivery tray 60 provided on the upper surface of the apparatus main body or passed to the two-surface apparatus 90 as indicated by the reference symbol r in FIG. 2.

In the printer 1 of the first embodiment, a process control operation (hereinafter, "pro-con operation") is executed whenever the power is switched on or every time a predetermined number of sheets of paper is printed to ensure an appropriate image density for each color. In this pro-con operation, a density detection patch (hereinafter, "reference pattern") is formed on each of the photosensitive drums 5Y, 5M, 5C, 5Bk. The reference pattern formed on each of the photosensitive drums 5Y, 5M, 5C, 5Bk is formed into a continuous tone reference pattern by successively switching the charging bias and developing bias. In other words, in the first embodiment, a line-form reference pattern in which the toner adhesion amount changes gradually is created along the surface migration direction of the photosensitive drums. Then, the reference pattern is detected by P sensors 30Y, 30M, 30C, 30Bk provided in each of the image-forming units 4Y, 4M, 4C, 4Bk.

Figure 4:
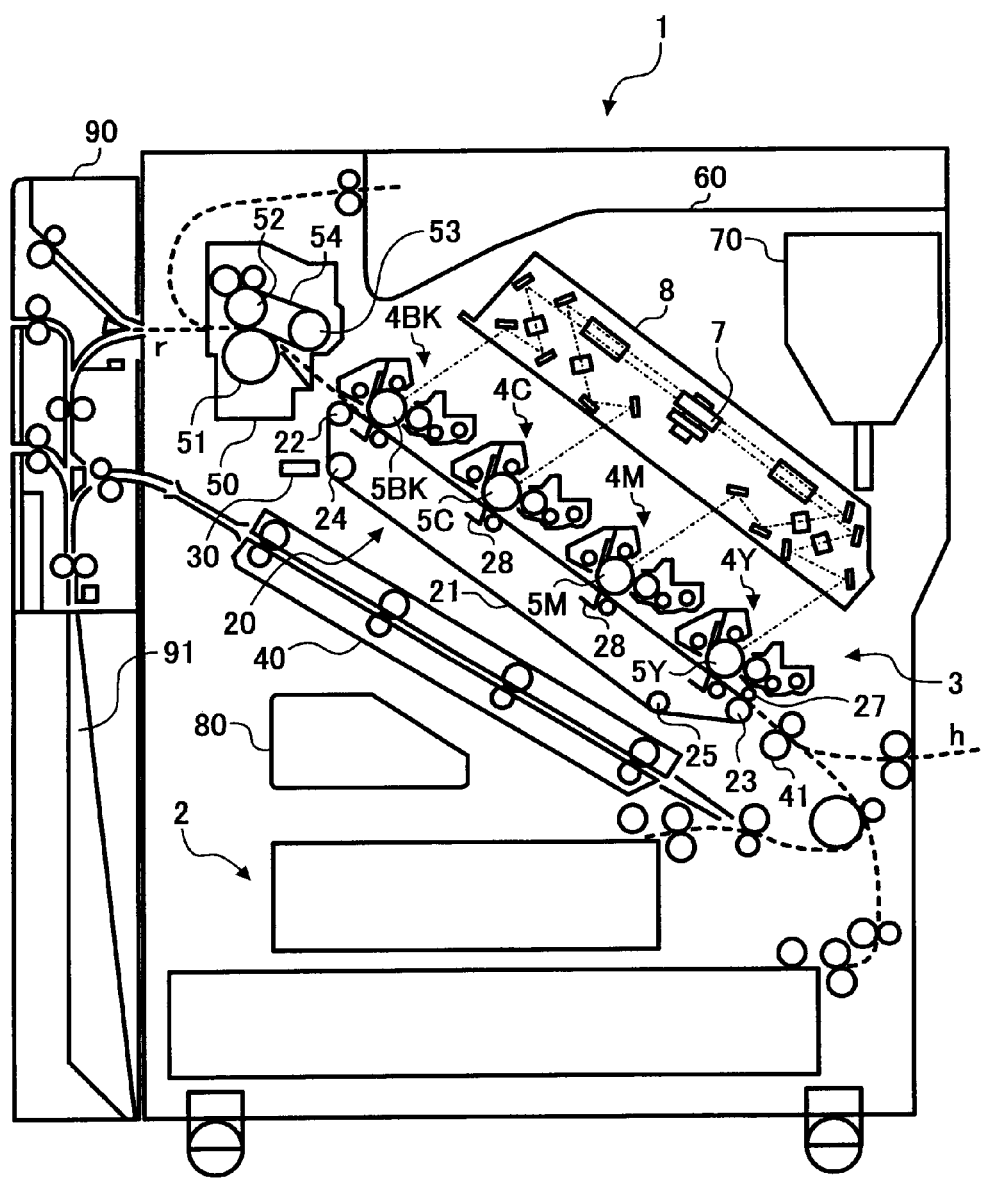
FIG. 4 is a cross section of the printer for illustrating another example of a layout of the P sensor.

Note that in the first embodiment, the reference pattern is detected on the photosensitive drum, but a constitution may be provided in which the reference pattern formed on the photosensitive drums 5Y, 5M, 5C, 5Bk is detected following transfer onto the transfer conveyor belt 21. In this case, a P sensor 30 is disposed opposite the transfer conveyor belt 21. More specifically, as shown in FIG. 4, for example, the P sensor 30 is disposed in a position opposing the tension roller 24 of the transfer conveyor belt apparatus 20. Since the image-forming units 4Y, 4M, 4C, 4Bk oppose the part of the transfer conveyor belt 21 which conveys recording paper, there is little space to spare for disposing the P sensor 30. However, as shown in FIG. 4, there is space to spare in the part of the transfer conveyor belt 21 which does not convey recording paper, and hence space increases or excessive complexity in equipment disposal caused by the disposal of the P sensor can be prevented. Note that when a constitution is provided in which the reference pattern is detected following transfer onto the transfer conveyor belt 21, reference patterns for each color are transferred onto the transfer conveyor belt 21 ensuring that the patterns do not overlap.

The P sensor 30 may double as position deviation detection means for the transfer conveyor belt 21. In other words, a predetermined mark may be provided on the transfer conveyor belt 21, and by detecting this mark, the P sensor 30 is able to detect deviation in the main scanning direction of the transfer conveyor belt 21.

In the following description, the color differentiating reference symbols Y, M, C, Bk have been omitted where appropriate.

Figure 1:
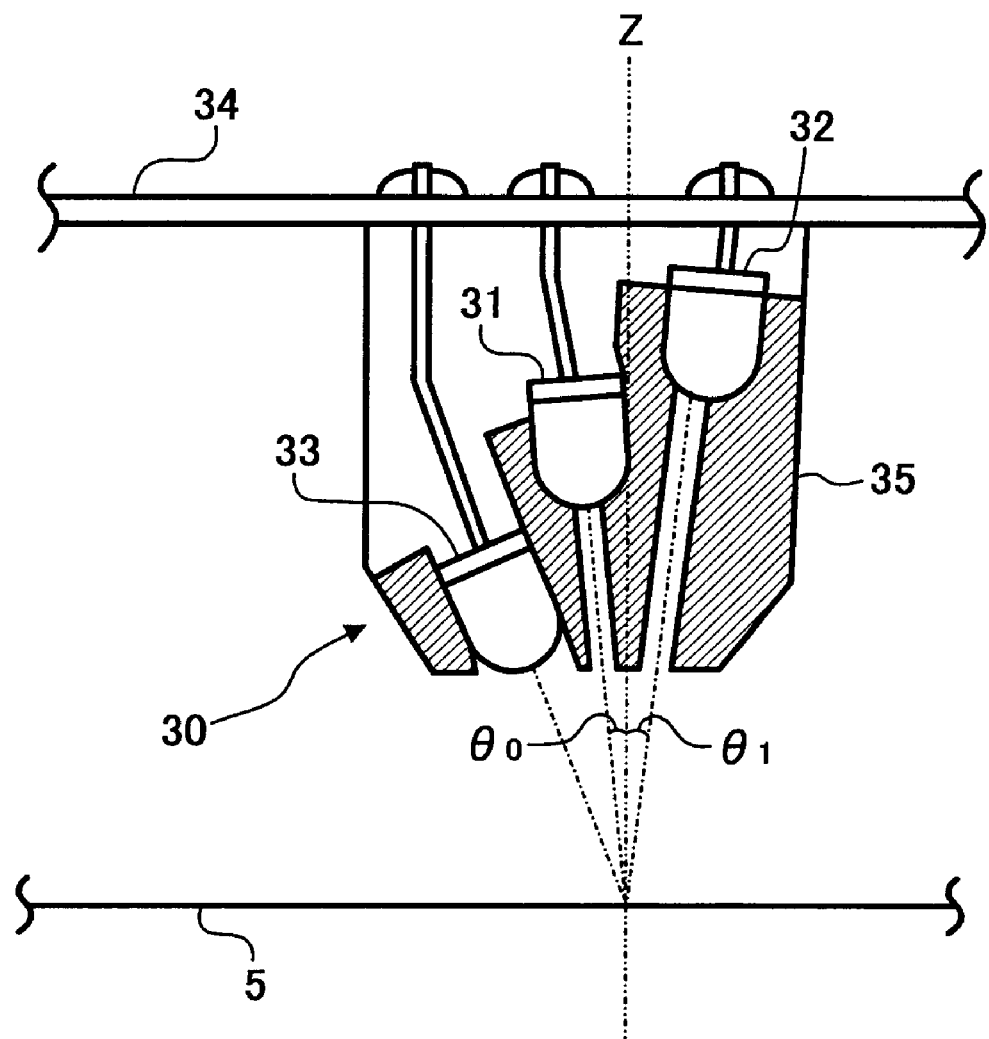
FIG. 1 is a cross section of a P sensor of each image-forming unit of a printer according to a first embodiment of the present invention.

FIG. 1 is a cross section of a P sensor 30 of each image-forming unit of the printer according to the first embodiment. The P sensor 30 of this embodiment is mainly constituted by a light-emitting element 31 serving as light emitting unit, a first light-receiving element 32 serving as first light receiving unit for receiving specular reflection light, and a second light-receiving element 33 serving as second light receiving unit for receiving diffuse reflection light. Each element 31, 32, 33 is mounted on a printed board 34 and sealed in a single package 35. A passage for securing an incident light path enabling incident light emitted from the light-emitting element 31 to reach the surface of the photosensitive drum 5, and a passage for securing a specular reflection light path enabling specular reflection light that is specularly reflected by the surface of the photosensitive drum 5 to reach the first light-receiving element 32 are respectively formed in the package 35. In this embodiment, a GaAs light emitting diode having a peak emission wavelength of 950 nm is used as the light-emitting element 31, and an Si phototransistor having a peak spectral sensitivity wavelength of 800 nm is used for the first light-receiving element 32 and second light-receiving element 33. Note that another light-receiving element such as a PD (photodiode) may be used for the first light-receiving element 32 and second light-receiving element 33 instead of an Si phototransistor.

In the first embodiment, continuous tone reference patterns are created on each of the photosensitive drums 5, and the toner adhesion amount of the reference patterns, which change gradually in toner density, is detected continuously by the P sensor 30. The outputs of the first light-receiving element 32 and second light-receiving element 33 in the P sensor 30 are transmitted to a control portion not shown in the drawings. In this control portion, the toner adhesion amount of the reference patterns is learned continuously on the basis of the amount of specular reflection light and diffuse reflection light obtained from these outputs, whereupon the learned toner adhesion amount is compared to a predetermined target adhesion amount. On the basis of the comparison result, the control portion functions as image density control unit to appropriately modify the intensity of the laser light from the optical fabrication apparatus 8, the charging bias that is applied to the charging roller 6, the developing bias that is applied to the developing sleeve 11, the amount of toner refilled into the developing machinery, and so on, as a result of which the image density is adjusted to a desired density.

In the first embodiment, fine particle toner having a weight average particle diameter of 8 micrometers or less is used. Accordingly, detection by the P sensor must be performed in regions having a large toner adhesion amount, as described above. It is therefore necessary to reduce the angle formed by adding the angle of incidence $\theta_0$ and the angle of specular reflection $\theta_1$ such that detection can be performed with sufficient sensitivity even in regions having a large toner adhesion amount.

Note that the weight average particle diameter of the toner may be measured by various methods, for example using a coulter counter. A Coulter Multisizer II (manufactured by Coulter Electronics, Inc.), for example, may be used as the coulter counter. By analyzing characteristics such as the quantity distribution and volume distribution, for example, on the basis of the measurement result obtained by such a coulter counter, the weight average particle diameter of the toner can be determined. An aqueous 1% sodium chloride solution adjusted using first-grade sodium chloride may be used as the electrolytic solution for the coulter counter measurement.

Further, the toner that is used in the first embodiment is formed by a so-called polymerization method, and has a form which is near to perfect sphericity and an average roundness of at least 0.93. As a result, the shadow factor increases as described above, and the sensitivity of the P sensor for detecting specular reflection light decreases in regions on the photosensitive drum surface having a large toner adhesion amount. It is therefore necessary to enable detection to be performed with sufficient sensitivity even in regions having a large toner adhesion amount.

Note that the average roundness of the toner is an average value of the roundness of each toner particle, and is measured using the following method. Measurement of the roundness of each toner particle was performed using a flow-type particle image analyzer FPIA-2100 manufactured by SYSMEX Corporation. To perform this measurement, first an aqueous 1% NaCl solution is adjusted using first-grade sodium chloride. The aqueous NaCl solution is then passed through a 0.45 filter to obtain 50 milliliters to 100 milliliters of liquid, whereupon 0.1 milliliter to 5 milliliters of surface active agent, preferably alkylbenzene sulfonate, is added thereto as a dispersing agent, and 1 milligram to 10 milligrams of a sample is also added. The resulting mixture is then subjected to a dispersing treatment in an ultrasonic dispersing machine for one minute, whereby the particle density is adjusted to between 5,000 particles/μl and 15,000 particles/μl such that a dispersed liquid is obtained. An image of this dispersed liquid is captured by a CCD camera, and a value obtained by dividing the circumference of a circle having the same area as the area of a two-dimensional projected image of a toner particle by the perimeter of the two-dimensional projected image of the toner particle is used as the roundness of each toner particle. Note that from the pixel accuracy of the CCD, toner in which the diameter (particle diameter) of a circle having the same area as the area of the two-dimensional projected image of the toner particle is at least 0.6 micrometer was deemed effective. The average roundness of the toner employs a value that is obtained by adding together the roundness of all of the toner particles within the measurement range after the roundness of each toner particle is obtained, and then dividing this value by the number of toner particles.

In the first embodiment, the light-emitting element 31 and the first light-receiving element 32 are disposed such that their relative positions deviate from one another in the normal direction of the photosensitive drum surface. By disposing the light-emitting element 31 and first light-receiving element 32 in this manner, they do not come into contact with each other even when disposed in proximity. In the first embodiment, as shown in the drawing, when an angle formed by a center line of the incident light path along which incident light emitted from the light-emitting element 31 travels to the surface of the photosensitive drum 5 and a normal direction Z of the photosensitive drum surface is set as the angle of incidence $\theta_0$, and the angle formed by a center line of the specular reflection light path of the specular reflection light that is specularly reflected by the photosensitive drum surface and the normal direction Z of the photosensitive drum surface is set as the angle of specular reflection $\theta_1$, then the angle obtained by adding the angle of incidence $\theta_0$ to the angle of specular reflection $\theta_1$ may be set to 25 degrees or less, which is difficult in a conventional P sensor, or preferably to 20 degrees or less.

Even with the constitution shown in FIG. 1, the light-emitting element 31 cannot be disposed so as to block the specular reflection light path, and hence there are limits on the extent to which the light-emitting element 31 and first light-receiving element 32 can be disposed in proximity. Hence in the first modified example, a constitution is employed in which the light-emitting element 31 and first light-receiving element 32 are not brought into mutual proximity, but instead, traveling direction changing unit for modifying the traveling direction of the light are provided on at least one of the incident light path and the specular reflection light path, and thus the angle obtained by adding the angle of incidence $\theta_0$ to the angle of specular reflection $\theta_1$ is set to 25 degrees or less.

Figure 5:
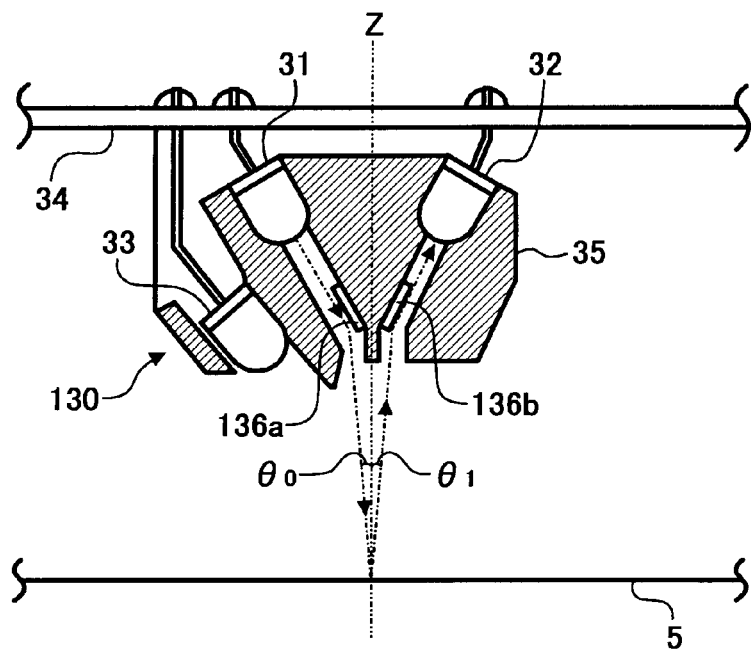
FIG. 5 is a cross section of a P sensor according to a first modification of the first embodiment.

FIG. 5 is a cross section of a P sensor 130 according to a first modification of the first embodiment. The light-emitting element 31, first light-receiving element 32, and second* light-receiving element 33 of the P sensor 130 of the first modified example are similar to those of the P sensor 30 shown in FIG. 1. However, in the P sensor 130 of the first modified example, the relative positions of the light-emitting element 31 and first light-receiving element 32 are aligned with each other in the normal direction of the photosensitive drum surface. In this condition, the angle obtained by adding the angle of incidence $\theta_0$ to the angle of specular reflection $\theta_1$ cannot be set to 25 degrees or less. Hence in the first modified example, reflective mirrors 136a, 136b serving as light reflecting members are provided at a point on the incident light path and the specular reflection light path respectively as the traveling direction changing unit.

By means of such a constitution, incident light emitted from the light-emitting element 31 is reflected by the reflective mirror 136a, and hence the traveling direction thereof is modified. As a result, the angle formed by the center line of the part of the incident light path directly before the incident light reaches the photosensitive drum surface and the normal direction Z can be set narrowly regardless of the angle formed by the center line of the part of the incident light path up to the reflective mirror 136a and the normal direction Z of the photosensitive drum surface. The specular reflection light that is specularly reflected by the photosensitive drum surface is also modified in traveling direction by being reflected on the reflective mirror 136b. As a result, similarly to the incident light, the angle formed by the center line of the part of the specular reflection light path directly after the specular reflection light is specularly reflected by the photosensitive drum surface and the normal direction Z can be set narrowly regardless of the angle formed by the center line of the part of the specular reflection light path from the reflective mirror 136b to the first light-receiving element 32 and the normal direction Z of the photosensitive drum surface. Hence according to the constitution of the first modified example, as long as the position and attitude of the reflective mirrors 136a, 136b are set appropriately, the angle obtained by adding together the angle of incidence $\theta_0$ and the angle of specular reflection $\theta_1$ can be set to 25 degrees or less regardless of where the light-emitting element 31 and first light-receiving element 32 are disposed.

Figure 6:
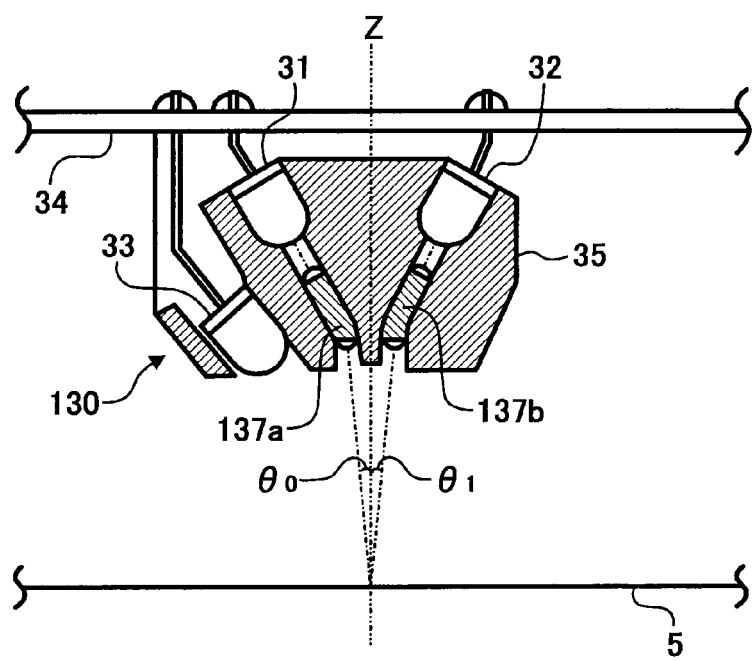
FIG. 6 is a cross section of the P sensor for illustrating another example of configuration.

Note that in the first modified example, a case was described in which light is reflected by the reflective mirrors 136a, 136b to alter the traveling direction of the light, but as shown in FIG. 6, the traveling direction of the light may be modified using optical guiding means such as optical fiber as light traveling direction changing unit 137a, 137b. In this case, the inner wall of the light guiding means functions as a light-reflecting member. The traveling direction of the light may also be modified using a diffraction grating or the like as light traveling direction changing unit.

Similarly to the first modified example, a second modified example employs a constitution in which the light-emitting element 31 and first light-receiving element 32 are not brought into mutual proximity, but instead, traveling direction changing unit for modifying the traveling direction of the light are provided on at least one of the incident light path and the specular reflection light path such that the angle obtained by adding the angle of incidence $\theta_0$ to the angle of specular reflection $\theta_1$ is set to 25 degrees or less.

Figure 7:
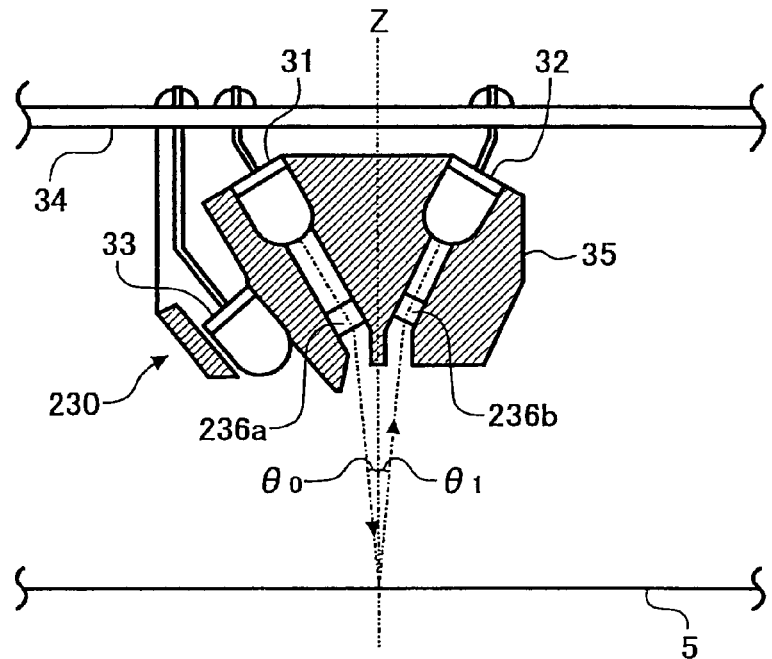
FIG. 7 is a cross section of a P sensor according to a second modification of the first embodiment.

FIG. 7 is a cross section of a P sensor 230 according to a second modification of the first embodiment. The basic constitution of the P sensor 230 in the second modified example is similar to that of the first modified example. In the P sensor 230 of the second modified example, however, refractive lenses 236a, 236b serving as photorefractive members are provided at a point on the incident light path and specular reflection light path respectively as traveling direction changing unit in place of the reflective mirrors 136a, 136b.

By means of such a constitution, incident light emitted from the light-emitting element 31 is refracted as it passes through the refractive lens 236a, and thus the traveling direction thereof is modified. Hence, the angle formed by the center line of the part of the incident light path directly before the incident light reaches the photosensitive drum surface and the normal direction Z can be set narrowly regardless of the angle formed by the center line of the part of the incident light path up to the refractive lens 236a and the normal direction Z of the photosensitive drum surface. The specular reflection light that is specularly reflected by the photosensitive drum surface is also modified in traveling direction by being refracted as it passes through the refractive lens 236b. As a result, similarly to the incident light, the angle formed by the center line of the part of the specular reflection light path directly after the specular reflection light is specularly reflected by the photosensitive drum surface and the normal direction Z can be set narrowly regardless of the angle formed by the center line of the part of the specular reflection light path from the refractive lens 236b to the first light-receiving element 32 and the normal direction Z of the photosensitive drum surface. Hence according to the constitution of the second modified example, similarly to that of the first modified example, as long as the position and attitude of the refractive lenses 236a, 236b are set appropriately, the angle obtained by adding together the angle of incidence $\theta_0$ and the angle of specular reflection $\theta_1$ can be set to 25 degrees or less regardless of where the light-emitting element 31 and first light-receiving element 32 are disposed.

Note that the traveling direction of the light can likewise be modified by disposing a convex lens and concave mirror serving as a light condensing member, or a concave mirror and convex lens serving as a light diffusing member, in the disposal position of the refractive lenses 236a, 236b so that the optical axis deviates from the center line of the incident light path and specular reflection light path. In so doing, a similar effect can be obtained.

The traveling direction of the light can also be modified when a convex lens and concave mirror serving as a light condensing member, or a concave mirror and convex lens serving as a light diffusing member, are disposed in the disposal position of the refractive lenses 236a, 236b so that the optical axis is inclined in relation to the center line of the incident light path and specular reflection light path. In so doing, a similar effect can be obtained.

If the light-emitting element 31 and first light-receiving element 32 are removed from the surface of the photosensitive drum 5, then the angle obtained by adding the angle of incidence $\theta_0$ to the angle of specular reflection $\theta_1$ can be set to 25 degrees or less without disposing the light-emitting element 31 and first light-receiving element 32 such that their relative positions deviate from one another in the normal direction of the photosensitive drum surface as shown in FIG. 1. In this case, however, the amount of light received by the first light-receiving element 32 is insufficient, and hence the sensitivity deteriorates. Thus in the third modified example, to prevent a deterioration in sensitivity when the light-emitting element 31 and first light-receiving element 32 are removed from the surface of the photosensitive drum 5, a light condensing member is disposed on at least one of the incident light path and specular reflection light path such that the optical axis aligns with the center line of that light path, whereby the angle obtained by adding together the angle of incidence $\theta_0$ and the angle of specular reflection $\theta_1$ can be set to 25 degrees or less.

Figure 8:
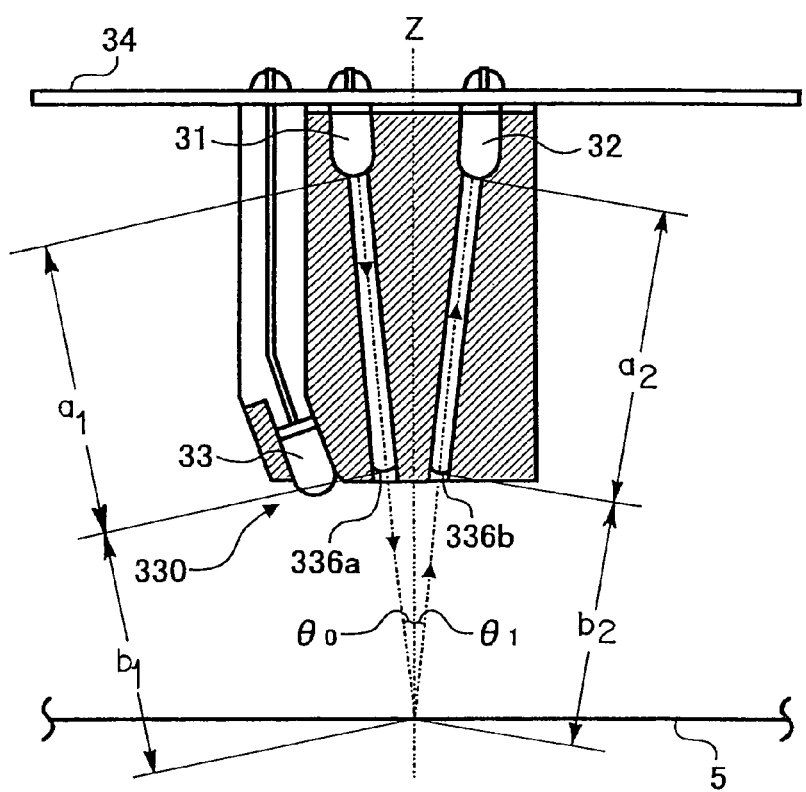
FIG. 8 is a cross section of a P sensor according to a third modification of the first embodiment.

FIG. 8 is a cross section of a P sensor 330 according to a third modification of the first embodiment. The light-emitting element 31, first light-receiving element 32, and second* light-receiving element 33 of the P sensor 330 of the third modified example are similar to those of the P sensor 30 shown in FIG. 1. In the P sensor 330 of the third modified example, however, the relative positions of the light-emitting element 31 and first light-receiving element 32 are aligned with each other in the normal direction of the photosensitive drum surface, and the distance from the photosensitive drum surface to the light-emitting element 31 and first light-receiving element 32 is great. In this condition, the amount of light received by the first light-receiving element 32 is insufficient, and hence the sensitivity deteriorates. Therefore, in the third modified example, a one-sided convex lens 336a is provided at a point on the incident light path as a light condensing member, and a one-sided concave lens 336b is provided at a point on the specular reflection light path as a light diffusing member.

In the third modified example, the one-sided convex lens 336a and one-sided concave lens 336b are disposed such that the flat surface side of each lens 336a, 336b opposes the photosensitive drum surface. In so doing, the lenses 336a, 336b can be cleaned easily when soiled by scattered toner. Note that here, "flat surface" is not strict, and also includes surfaces having a sufficiently large curvature to facilitate cleaning.

Also in the third modified example, when the distance from the light-emitting element 31 to the one-sided convex lens 336a is set as $a_1$, the distance from the one-sided convex lens 336a to the photosensitive drum surface is set as $b_1$, the focal distance of the one-sided convex lens 336a is set as $f_1$, the distance from the one-sided concave lens 336b to the first light-receiving element 32 is set as $a_2$, the distance from the photosensitive drum surface to the one-sided concave lens 336b is set as $b_2$, and the focal distance of the one-sided concave lens 336b is set as $f_2$, the one-sided convex lens 336a and one-sided concave lens 336b are disposed so as to satisfy the two expressions shown in (1). As a result, the specular reflection light of the incident light from the light-emitting element 31 can be condensed in the one-sided concave lens 336b. The condensed specular reflection light can then be condensed by the one-sided concave lens 336b so as to be directed toward the first light-receiving element 32. Thus the transmission efficiency of the specular reflection light to the first light-receiving element 32 can be improved. Moreover, an effect of widening the margin for irregularities in the attachment angle and so on of the one-sided convex lens 336a and one-sided concave lens 336b is obtained. Note that these effects can only be obtained when at least one of the two expressions shown in following equations (1) are satisfied.

$$1/a_1 + 1/(b_1+b_2) = 1/f_1$$

$$1/a_2 + 1/(b_1+b_2) = 1/f_2 \quad (1)$$

Figure 9:
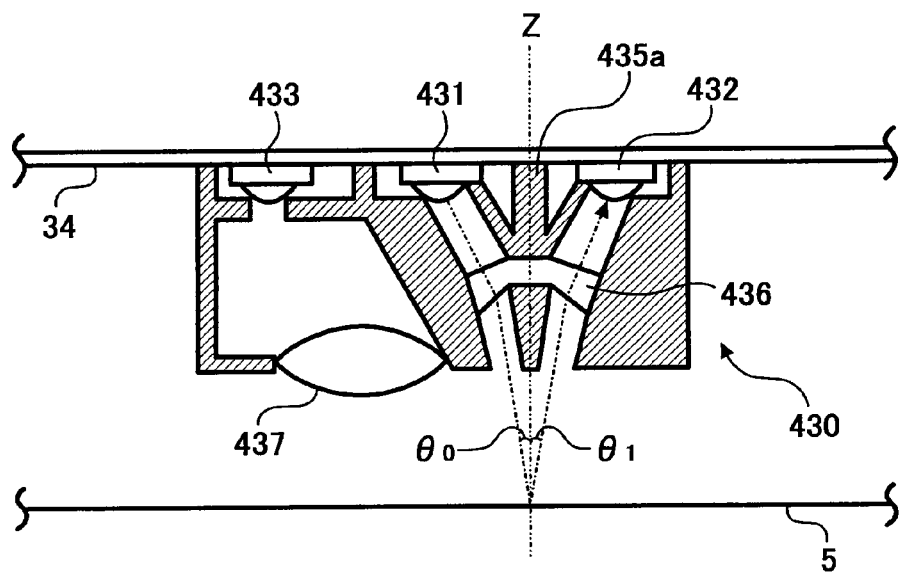
FIG. 9 is a cross section of a P sensor according to a fourth modification of the first embodiment.

FIG. 9 is a cross section of a P sensor 430 according to a fourth modification of the first embodiment. A light-emitting element 431, first light-receiving element 432, and second* light-receiving element 433 serving as the optical elements of the P sensor 430 in the fourth modified example are constituted as Surface Mount Devices (SMDs) that are surface mounted on a printed board 34. The element surface of each element 431, 432, 433 faces a normal direction of the surface of the printed board 34. Note that only the outward form of the elements 431, 432, 433 is constituted as an SMD, and the content thereof is identical to the elements of the P sensor 30 shown in FIG. 1. By constituting the light-emitting element 431 and first light-receiving element 432 as SMDs, the elements themselves can be reduced in size, the intervals between the elements can be narrowed, and so on. In other words, the angle obtained by adding the angle of incidence $\theta_0$ to the angle of specular reflection $\theta_1$ can be set to 25 degrees or less.

Even when the elements are constituted as SMDs as in the fourth modified example, the light-emitting element 431 and first light-receiving element 432 can be only be brought into proximity until they contact one another, and hence the extent to which the elements can be brought into proximity is limited. Hence in the fourth modified example, a shared lens 436 serving as a photorefractive member is provided on the incident light path and specular reflection light path as route varying means so that the angle obtained by adding the angle of incidence $\theta_0$ to the angle of specular reflection $\theta_1$ can be reduced even further. The shared lens 436 is disposed such that the optical axis thereof deviates from the center line of the incident light path and specular reflection light path, and hence the traveling direction of the light passing through each of the light paths can be modified. Hence according to the constitution of the fourth modified example, as long as the position, attitude, and so on of the shared lens 436 is set appropriately, the angle obtained by adding the angle of incidence $\theta_0$ to the angle of specular reflection $\theta_1$ can be set narrowly without disposing the light-emitting element 431 and first light-receiving element 432 excessively close to each other.

Note that in the fourth modified example, the second light-receiving element 433 for receiving diffuse reflection light is also surface mounted and disposed in a position removed from the photosensitive drum surface. Hence the amount of diffuse reflection light that is received by the second light-receiving element 433 may be insufficient. Therefore, in the fourth modified example, a convex lens 437 is provided on the diffuse reflection light path for the diffuse reflection light received by the second light-receiving element 433 such that the optical axis thereof deviates from the center line of the light path. In so doing, diffuse reflection light that results when incident light is diffusely reflected by the toner can be condensed toward the second light-receiving element 433 by the convex lens 437. Thus a sufficient amount of diffuse reflection light to be received in the second light-receiving element 433 can be secured, enabling appropriate image density control. Note that in the fourth modified example, when the distance from the start point of the diffuse reflection light path, or in other words the photosensitive drum surface, to the convex lens 437 is set as a, the distance from the convex lens 437 to the end point of the diffuse reflection light path, or in other words the second light-receiving element 33, is set as b, and the focal distance of the convex lens 437 is set as f, the convex lens 437 is disposed so as to satisfy the expression shown in (2). Thus the transmission efficiency of the diffuse reflection light from the photosensitive drum surface to the second light-receiving element 33 can be improved.

$$1/a + 1/b = 1/f \quad (2)$$

Further, in the fourth modified example, the light-emitting element 431 and first light-receiving element 432 are surface mounted on the same surface of the same printed board 34, and hence unless a shield is provided on the segment linking the optical elements, incident light emitted from the light-emitting element 431 is received directly by the first light-receiving element 432 such that accurate detection cannot be performed. In the fourth modified example, a light-shielding wall 435a is provided as light shielding means on the segment linking the light-emitting element 431 and first light-receiving element 432. Note that a mounted device such as a condenser or coil that is mounted on the printed board 34 may be used instead of the light-shielding wall 435a. Direct reception of incident light emitted from the light-emitting element 431 by the first light receiving unit 432 may also be suppressed by providing a through hole in the surface of the printed board at the segment linking the light-emitting element 431 and first light receiving unit 432 instead of providing such light shielding means. By means of such a constitution, direct reception in the first light receiving unit 432 of the reflected light that results when incident light from the light-emitting element 431 is reflected on the surface of the printed board can be suppressed, and as a result, accurate detection is possible.

Figure 10:
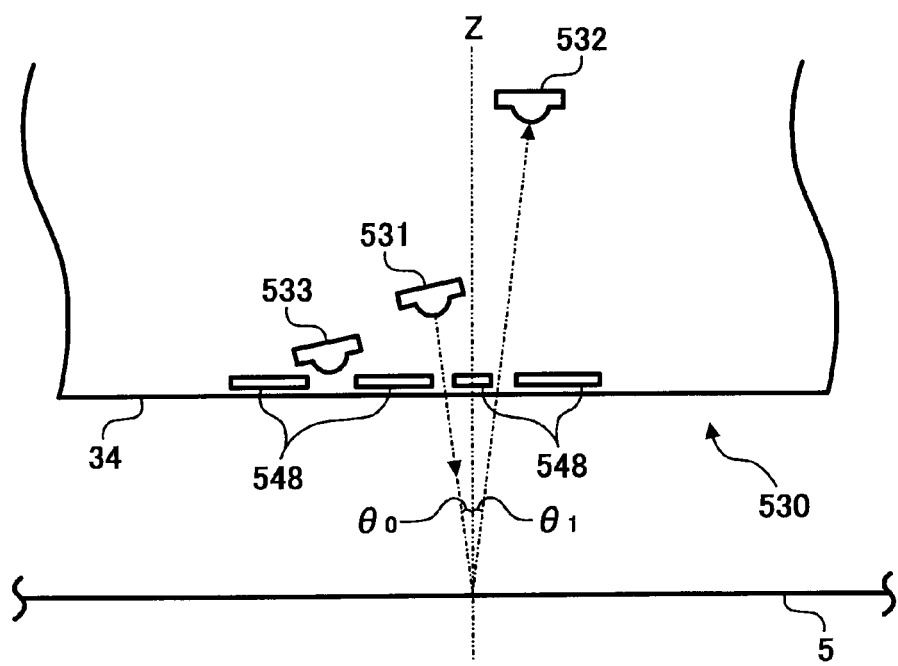
FIG. 10 is a schematic of a P sensor according to a fifth modification of the first embodiment.

FIG. 10 is a schematic of a P sensor 530 according to a fifth modification of the first embodiment. A light-emitting element 531, first light-receiving element 532, and second* light-receiving element 533 serving as the optical elements of the P sensor 530 in the fifth modified example are constituted as SMDs similarly to those of the fourth modified example, and are surface mounted on the printed board 34. However, the surface of each element faces a parallel direction to the surface direction of the printed board 34. Note that only the outward form of the elements 531, 532, 533 is constituted as an SMD, and the content thereof is identical to the elements of the P sensor 30 shown in FIG. 1. By constituting the light-emitting element 531 and first light-receiving element 532 as SMDs, the angle obtained by adding the angle of incidence $\theta_0$ to the angle of specular reflection $\theta_1$ can be set to 25 degrees or less, similarly to the fourth modified example described above.

Also similarly to the fourth modified example, a light diffusing member and light condensing member serving as route varying means may be disposed on the incident light path and specular reflection light path such that the optical axis thereof deviates from the center line of the incident light path and specular reflection light path. By means of such a constitution, the angle obtained by adding the angle of incidence $\theta_0$ to the angle of specular reflection $\theta_1$ can be set narrowly without disposing the light-emitting element 531 and first light-receiving element 532 excessively close to each other.

Also in the fifth modified example, the first light-receiving element 532 is disposed at a dead angle of the light-emitting element 531*(a position which incident light cannot reach directly) to prevent incident light emitted from the light-emitting element 531 from being directly received by the first light-receiving element 532. Note that similarly to the fourth modified example, direct reception of incident light emitted from the light-emitting element 531 by the first light receiving element 532 may also be suppressed by providing shielding means such as a light-shielding wall or mounted device on the segment linking the light-emitting element 531 and first light-receiving element 532, or by providing a through hole in the surface of the printed board at the segment linking the light-emitting element 531 and first light receiving element 532.

Further, in the fifth modified example the light paths are parallel to the surface direction of the printed board, and hence when mounted devices are placed on the light paths, the light is blocked by the mounted devices such that the amount of light received by the first light-receiving element 532 is insufficient. Thus in the fifth modified example, the mounted devices on the printed board 34 are mounted in positions which do not block the incident light path and specular reflection light path. Also in the fifth modified example, a light-shielding plate 548 that is cut away at the part which forms the incident light path is provided on the printed board 34. This cut-away portion exhibits a so-called light-squeezing effect.

Figure 11:
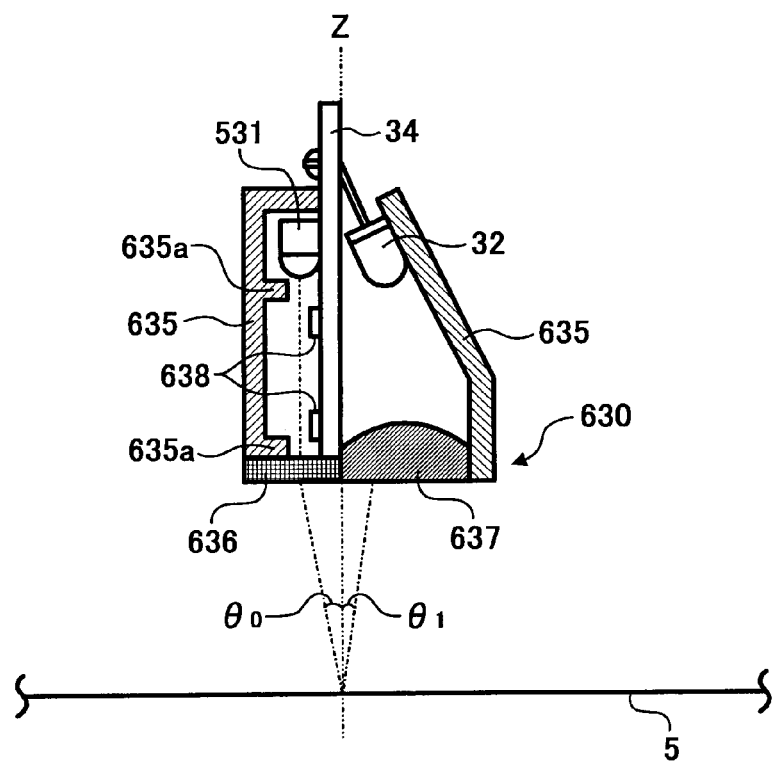
FIG. 11 is a cross section of a P sensor according to a sixth modification of the first embodiment.

FIG. 11 is a cross section of a P sensor 630 according to a sixth modification of the first embodiment. The light-emitting element 531 serving as an optical element of the P sensor 630 in the sixth modified example is constituted as an SMD, similarly to the fifth modified example described above, and the element surface thereof is surface mounted so as to face a parallel direction to the surface direction of the printed board 34. The first light-receiving element 32 serving as an optical element of the P sensor 630 in the sixth modified example is identical to the first light-receiving element of the P sensor 30 shown in FIG. 1. Note that the second light-receiving element for receiving diffuse reflection light is omitted from the drawing. This constitution also allows the angle obtained by adding the angle of incidence $\theta_0$ to the angle of specular reflection $\theta_1$ to be set to 25 degrees or less.

Further, in the sixth modified example a condensing lens 636 serving as a light condensing member is disposed on the incident light path as route varying means and a photorefractive member. In this constitution, incident light that travels along the surface of the printed board 34 from the light-emitting element 531 is refracted by the condensing lens 636 and condensed at the illumination target on the photosensitive drum surface. Further, a condensing lens 637 serving as a light condensing member is disposed on the specular reflection light path as route varying means and a photorefractive member. In the sixth modified example, when the distance from the start point of the incident light path, or in other words the light-emitting element 531, to the condensing lens 636, and the distance from the start point of the specular reflection light path, or in other words the photosensitive drum surface, to the condensing lens 637 are set as a, the distance from the condensing lens 636 to the end point of the incident light path, or in other words the photosensitive drum surface, and the distance from the condensing lens 637 to the end point of the specular reflection light path, or in other words the first light-receiving element 32, are set as b, and the focal distance of the condensing lenses 636, 637 is set as f, the condensing lenses 636, 637 are disposed so as to satisfy the expression shown in (2). Thus the transmission efficiency of the incident light from the light-emitting element 531 to the illumination target on the photosensitive drum surface, and the transmission efficiency of the specular reflection light from the photosensitive drum surface to the first light-receiving element 32 can be improved respectively.

By means of such a constitution, even if incident light emitted from the light-emitting element 531 diverges somewhat before reaching the condensing lens 636, the incident light is condensed toward the illumination target on the photosensitive drum surface by the condensing lens 636. Thus the illumination target on the photosensitive drum surface can be irradiated with a sufficient amount of incident light even when the light-emitting element 531 is removed from the photosensitive drum surface. The specular reflection light that is specularly reflected by the photosensitive drum surface is also condensed toward the first light-receiving element 32 by the condensing lens 637 even when the specular reflection light diverges somewhat before reaching the condensing lens 637. Thus a sufficient amount of reflection light can be received in the first light-receiving element 32 even when the first light-receiving element 32 is removed from the photosensitive drum surface. Hence, according to the constitution of the sixth modified example, the amount of light received in the first light-receiving element 32 is not insufficient even when the light-emitting element 531 and first light-receiving element 32 are disposed at a remove from the photosensitive drum surface. As a result, the angle obtained by adding the angle of incidence $\theta_0$ to the angle of specular reflection $\theta_1$ can be set to 25 degrees or less without causing a reduction in sensitivity.

Further, the part of the specular reflection light path from the condensing lens 637 to the first light-receiving element 32 is surrounded by the surface of the printed board 34 and the inner wall face of a case 635, and these surfaces act as reflection surfaces for reflecting light. Hence the part of the specular reflection light that is not directed toward the first light-receiving element 32 from the condensing lens 637 is reflected repeatedly on the surface of the printed board 34 and inner wall face of the case 635, and as a result, is received in the first light-receiving element 32. Accordingly, a sufficient amount of light can be received securely in the first light-receiving element 32.

Also in the sixth modified example, the printed board 34 exists on the segment linking the light-emitting element 531 and first light-receiving element 32, and hence incident light emitted from the light-emitting element 531 is not received directly in the first light-receiving element 32.

In the sixth modified example, the incident light path and specular reflection light path are substantially parallel to the surface direction of the printed board 34, and hence the amount of light received in the first light-receiving element 532 becomes insufficient when light is blocked by a mounted device on the light path. Thus in the sixth modified example, either no mounted devices are mounted on the printed board opposite the light paths, or the mounted device is constituted as a flat SMD 638.

Further, in the sixth modified example a convex portion 635a is formed on the inner wall face of the case 635 in order to obtain a light-squeezing effect between the convex portion 635a and the printed board 34. In so doing, an incident light-squeezing effect is obtained between the convex portion 635a and the printed board. Here, the light emitting position of the light-emitting element 531 requires a certain degree of height from the surface of the printed board 34, and hence the incident light passes through a position that is somewhat removed from the surface of the printed board 34. As a result, the squeezing effect between the convex portion 635a and the printed board surface is sometimes insufficient. Therefore, in the sixth modified example the SMD 638 is surface mounted on the surface of the printed board 34 opposite the convex portion 635a on the inner wall of the case 635. In so doing, the incident light-squeezing effect between the convex portion 635a and the surface of the SMD 638 can be improved. Note that this improvement in the squeezing effect may be obtained similarly by providing a separate light-shielding member or the like on the printed board 34 in place of a device that is mounted on the printed board 34. However, by obtaining the improvement through the use of the SMD 638 serving as a device that is mounted on the printed board 34, as in the sixth modified example, the costs required for providing the light-shielding member or the like can be eliminated.

Note that in the sixth modified example, the diaphragm diameter of the incident light from the light-emitting element 531 is set to be larger than the diaphragm diameter of the specular reflection light entering the light-receiving element 532, although this is not indicated in the drawing. In so doing, the resolution of the line-form reference pattern formed on the photosensitive drum is enhanced, and the toner adhesion amount can be detected in even more detail.

Figure 12A:
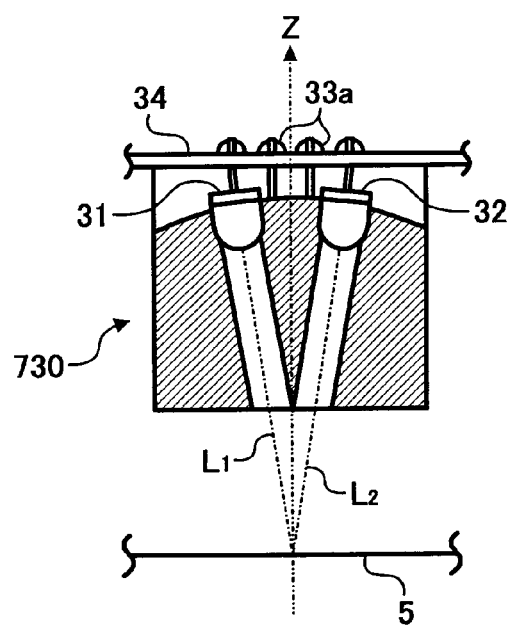
FIG. 12A is a cross section of a P sensor according to a seventh modification of the first embodiment, cut along a first virtual plane including an incident light path and a specular reflection light path.
Figure 12B:
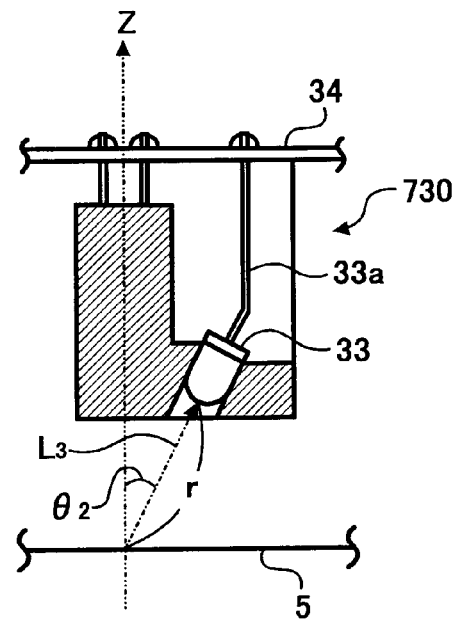
FIG. 12B is a cross section of a P sensor according to a seventh modification of the first embodiment, cut along a second virtual plane including normal of a surface of a photosensitive drum at a reflection point O, and is orthogonal to the first virtual plane.

As described above, the distance (hereinafter, "diffuse reflection light receiving distance") from the point of reflection on the photosensitive drum surface to the light receiving face of the second light-receiving element for receiving diffuse reflection light must be made short in order to improve the light receiving efficiency of diffuse reflection light. Also, the angle (hereinafter, "diffuse reflection light receiving angle") formed by the surface normal direction of the reflection point on the photosensitive drum surface to the center line of an diffuse reflection light path for the diffuse reflection light that is received by the second light-receiving element must be narrowed. However, in all of the P sensors 30, 130, 230, 330, 430, 530, 630 described above, the second light-receiving element 33, 433, 533 is disposed within a virtual plane including the incident light path and the specular reflection light path, and hence the second light-receiving element 33, 433, 533 is obstructed by the light-emitting element or first light-receiving element, as a result of which the diffuse reflection light receiving distance cannot be reduced sufficiently in length, and the diffuse reflection light receiving angle cannot be sufficiently narrowed. FIG. 12A and FIG. 12B are cross sections of a P sensor 730 according to a seventh modification of the first embodiment. Note that FIG. 12A is a sectional view severed along a first virtual plane which includes the incident light path along which the incident light $L_1$ from the light-emitting element 31 travels to the surface of the photosensitive drum 5, and the specular reflection light path along which the specular reflection light $L_2$ from the photosensitive drum surface travels to the first light-receiving element 32. FIG. 12B is a sectional view severed along a second virtual plane which includes the normal of the photosensitive drum surface at a reflection point O, and which is orthogonal to the first virtual plane.

Figure 13:
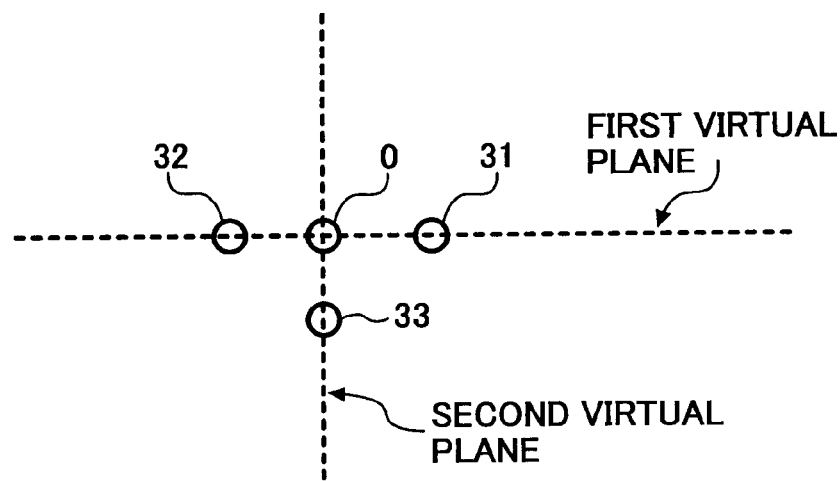
FIG. 13 is a schematic for illustrating a layout of a light-emitting element, a first light-receiving element, and a second light-receiving element seen from normal direction to the surface of the photosensitive drum at the reflection point O.

The light-emitting element 31, first light-receiving element 32, and second* light-receiving element 33 of the P sensor 730 in the seventh modified example are similar to those of the P sensor 30 shown in FIG. 1. However, in the P sensor 730 of the seventh modified example, the second light-receiving element 33 is disposed outside of the first virtual plane including the incident light path and specular reflection light path. More specifically, in the seventh modified example, the second light-receiving element 33 is disposed on the second virtual plane which includes the normal of the photosensitive drum surface and is orthogonal to the first virtual plane at the reflection point O, as shown in FIG. 13. By means of this disposal configuration, the diffuse reflection light receiving distance r can be shortened sufficiently and the diffuse reflection light receiving angle $\theta_2$ can be narrowed sufficiently regardless of where the light-emitting element 31 and first light-receiving element 32 are disposed.

Also in the seventh modified example, the light-emitting element 31 and first light-receiving element 32 are disposed at a remove from the photosensitive drum surface in order to narrow the angle obtained by adding the angle of incidence $\theta_0$ to the angle of specular reflection $\theta_1$, as shown in FIG. 12. Accordingly, the printed board 34 on which the light-emitting element 31, first light-receiving element 32, and second light-receiving element 33 are mounted is also disposed at a remove from the photosensitive drum surface. As described above, however, the second light-receiving element 33 for receiving diffuse reflection light is preferably disposed as close to the reflection point O on the photosensitive drum surface as possible. Hence in the seventh modified example, a lead-type element having a lead wire that is soldered to the printed board 34 is used as the second light-receiving element 33. In so doing, the second light-receiving element 33 can be disposed freely, regardless of where the printed board 34 is disposed, by extending the lead wire. Hence, the second light-receiving element 33 alone can be disposed in proximity to the photosensitive drum surface, even when the printed board 34 is disposed at a remove from the photosensitive drum surface, by extending the lead wire.

Note that in conventional cases where the second light-receiving element 33 is disposed within the first virtual plane, the diffuse reflection light receiving angle can be reduced sufficiently or to zero if the second light-receiving element 33 is disposed between the light-emitting element 31 and first light-receiving element 32, and hence the light receiving efficiency of diffuse reflection light can be improved. In this case, however, the elements 31, 32, 33 must be prevented from blocking each others' light paths, and moreover, the distance between the light-emitting element 31 and the first light-receiving element 32 cannot be reduced due to obstruction by the second light-receiving element 33. As a result, the shadow factor described above increases, and the detection sensitivity for specular reflection light deteriorates. According to the constitution of the seventh modified example, on the other hand, the diffuse reflection light receiving distance can be shortened sufficiently and the diffuse reflection light receiving angle can be narrowed sufficiently regardless of where the light-emitting element 31 and first light-receiving element 32 are disposed, and hence the detection sensitivity of diffuse reflection light can be improved by raising the light receiving efficiency of diffuse reflection light without causing a decrease in the detection sensitivity of specular reflection light.

In the P sensor of the eighth modified example, similarly to that of the seventh modified example described above, the second light-receiving element 33 is disposed on the second virtual plane which includes the normal of the photosensitive drum surface and is orthogonal to the first virtual plane at the reflection point O. Hence the diffuse reflection light receiving distance r can be shortened sufficiently and the diffuse reflection light receiving angle $\theta_2$ can be narrowed sufficiently regardless of where the light-emitting element 31 and first light-receiving element 32 are disposed.

Figure 14:
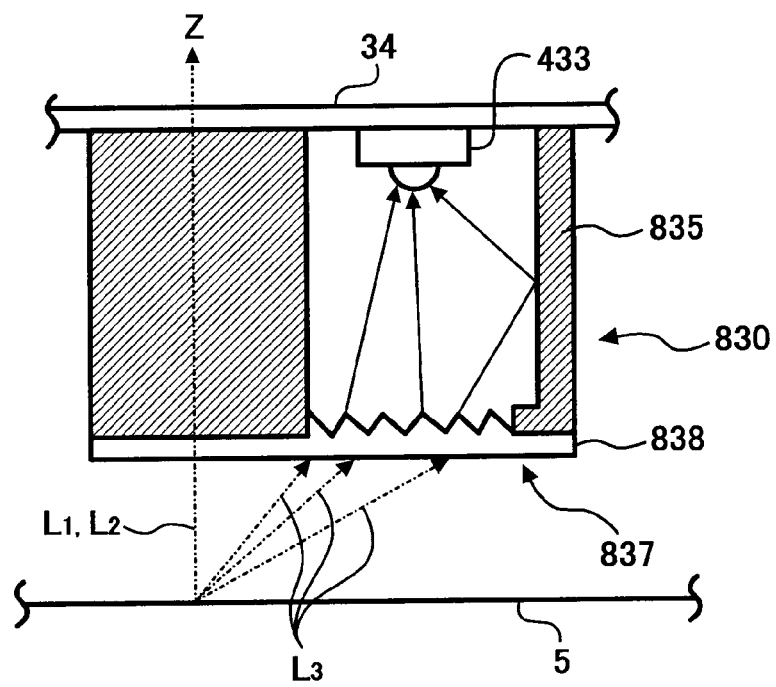
FIG. 14 is a cross section of a P sensor according to an eighth modification of the first embodiment, cut along the second virtual plane including the normal of the surface of the photosensitive drum at the reflection point O, and is orthogonal to the first virtual plane.

FIG. 14 is a cross section of a P sensor 830 according to an eighth modification of the first embodiment, cut along the second virtual plane including the normal of the photosensitive drum surface at the reflection point O, and which is orthogonal to the first virtual plane including the incident light path and specular reflection light path.

The light-emitting element (not shown), first light-receiving element (not shown)*, and second light-receiving element 433* of the P sensor 830 of the eighth modified example are constituted as SMDs, similarly to those of the fourth modified example, and the element surfaces thereof are surface mounted so as to face a normal direction in relation to the surface of the printed board 34. The P sensor 830 comprises a casing 835 which surrounds a region of the diffuse reflection light path, along which diffuse reflection light received by the second light-receiving element 433 travels, that is adjacent to the second light-receiving element 433. A dust-proof cover 838 constituted by a Fresnel lens 837 is provided at an inlet opening for diffuse reflection light to enter the casing 835. The part of the Fresnel lens 837 corresponding to the inlet opening serves as a light transmitting member and a light condensing member. By means of the dust-proof cover 838, foreign matter such as scattered toner can be prevented from infiltrating the interior of the casing 835, and hence foreign matter can be prevented from becoming transferred to the second light-receiving element 433. Diffuse reflection light from the photosensitive drum surface enters the interior of the casing 835 through the Fresnel lens 837. The inner wall of the casing 835 serves as a reflection surface which reflects the diffuse reflection light. More specifically, the inner wall of the casing 835 is painted white or formed by a reflective mirror. Thus at least a part of the diffuse reflection light passing through the Fresnel lens 837 is reflected on the inner wall surface of the casing 835 and condensed into the second light-receiving element 433. Hence a sufficient amount of diffuse reflection light can be secured in the second light-receiving element 433. Note that since the diffuse reflection light is infrared light, the inner wall surface of the casing 835 may be formed from any material which is unlikely to absorb infrared light, and is therefore not limited to the constitution of the eighth modified example.

In the P sensor of the ninth modified example, similarly to the seventh and eighth modified examples described above, the second light-receiving element 33 is disposed on the second virtual plane which includes the normal of the photosensitive drum surface and is orthogonal to the first virtual plane at the reflection point O. Hence the diffuse reflection light receiving distance r can be shortened sufficiently and the diffuse reflection light receiving angle $\theta_2$ can be narrowed sufficiently regardless of where the light-emitting element 31 and first light-receiving element 32 are disposed.

Figure 15:
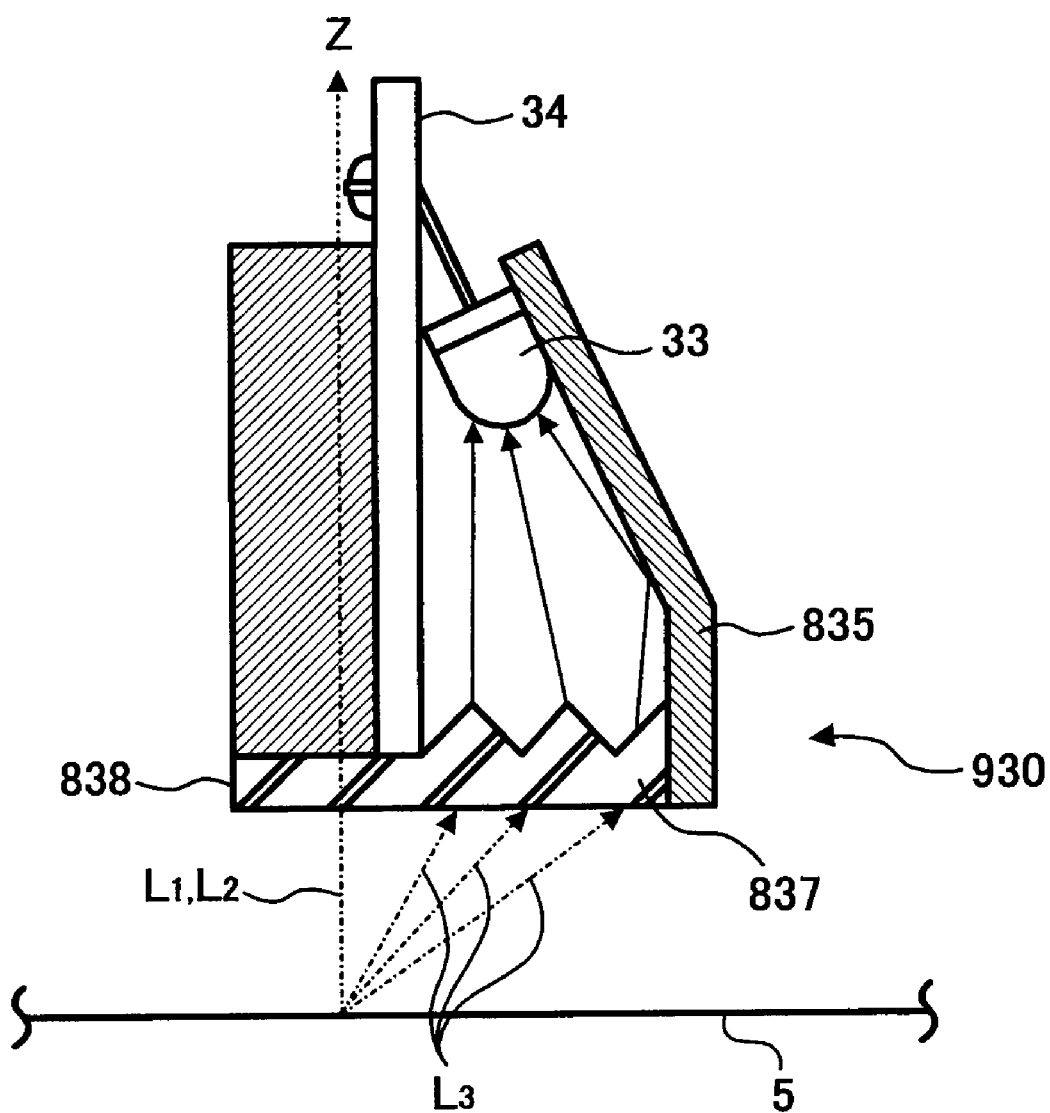
FIG. 15 is cross section of a P sensor according to a ninth modification of the first embodiment, cut along the second virtual plane including the normal of the surface of the photosensitive drum at the reflection point O, and is orthogonal to the first virtual plane.

FIG. 15 is cross section of a P sensor 930 according to a ninth modification of the first embodiment, cut along the second virtual plane including the normal of the surface of the photosensitive drum at the reflection point O, and is orthogonal to the first virtual plane.

The light-emitting element 531 (not shown) and first light-receiving element 532 (not shown), which are optical elements of the P sensor 930 of the ninth modified example, are constituted as SMDs, similarly to the fifth modified example, and the element surfaces thereof are surface mounted so as to face a parallel direction to the surface direction of the printed board 34. Meanwhile, the second light-receiving element 33, which serves as an optical element of the P sensor 930 of the ninth modified example, is similar to the first light-receiving element of the P sensor 30 shown in FIG. 1. In the ninth modified example, the light-emitting element 531 and first light-receiving element 532 are mounted onto the same surface of the printed board 34, whereas the second light-receiving element 33 is mounted on the opposite surface of the printed board 34. In such a constitution, the printed board 34 exists on the segment linking the light-emitting element 531 and the second light-receiving element 33, and hence incident light emitted from the light-emitting element 531 is not received directly in the second light-receiving element 33.

Further, in the ninth modified example, a reasonably-priced single-surface substrate is used as the printed board 34 having the light-emitting element 531 and first light-receiving element 532 mounted on the same surface, and hence costs are reduced. Note that since the lead wire of the second light-receiving element 33 is soldered to the opposite surface of the substrate surface on which second light-receiving element 33 is mounted, soldering must be performed on the substrate surface side on which the light-emitting element 531 and first light-receiving element 532 are mounted. In this case, if the lead wire is drawn near to the light-emitting element 531 and first light-receiving element 532, flax may fly up during soldering and soil the element surface of the light-emitting element 531 and first light-receiving element 532. In the ninth modified example, however, the lead wire of the second light-receiving element 33 is drawn out to a position removed from the light-emitting element 531 and first light-receiving element 532, and hence there is no danger of the element surface becoming soiled during soldering.

Further, the P sensor 930 of the ninth modified example is also provided with the dust-proof cover 838 constituted by the Fresnel lens 837 at the inlet opening for diffuse reflection light to enter the casing 835, similarly to the eighth modified example, and the inner wall of the casing 835 similarly serves as a reflection surface for reflecting diffuse reflection light. Hence at least a part of the diffuse reflection light that passes through the Fresnel lens 837 is reflected on the inner wall surface of the casing 835 and condensed in the second light-receiving element 33, thus enabling a sufficient amount of diffuse reflection light to be received securely in the second light-receiving element 33.

The P sensors 30, 130, 230, 330, 430, 530, 630, 730, 830, 930 serving as the optical sensor of the first embodiment comprise at least one light-emitting element 31, 431, 531 serving as light emitting unit, the first light-receiving element 32, 432, 532 serving as light receiving unit for receiving the specular reflection light $L_2$ that is generated when the incident light $L_1$ that is emitted from the light-emitting element is specularly reflected by a photosensitive drum surface serving as an illumination object, and the second light-receiving element 33, 433, 533 serving as second light receiving unit for receiving diffuse reflection light generated when the incident light $L_1$ emitted from the light-emitting element is diffusely reflected by toner on the photosensitive drum surface. Further, the angle formed by the center line of the incident light path, along which incident light from the light-emitting element 31, 431, 531 travels to the photosensitive drum surface, directly before the incident light reaches the photosensitive drum surface, and the center line of the specular reflection light path, along which specular reflection light from the photosensitive drum surface travels to the first light-receiving element 32, 432, 532, directly after the specular reflection light is reflected on the photosensitive drum surface is constituted to be no more than 25°, and preferably no more than 20°. As a result, the shadow factor decreases, and hence even when a large amount of toner is transferred to the photosensitive drum surface, the toner adhesion amount can be detected with sufficient sensitivity, leading to a widening of the range in which toner adhesion amounts can be detected with good sensitivity.

Further, the P sensors 130, 230, 430, 630 of the first, second, fourth, and sixth modified examples described above comprise traveling direction changing unit for modifying the traveling direction of the light on at least one of the incident light path and specular reflection light path. For example, in the first modified example, the traveling direction changing unit are constituted by the reflective mirrors 136a, 136b serving as a light reflecting member for reflecting light. In the second modified example, the traveling direction changing unit are constituted by the refractive lenses 236a, 236b serving as a photorefractive member for refracting light. In the fourth modified example, the traveling direction changing unit are constituted by the shared lens 436 serving as a light condensing member or light diffusing member disposed such that the optical axis thereof deviates from the center line of the light paths. In the sixth modified example, the traveling direction changing unit are constituted by the condensing lens 637 serving as a light condensing member disposed such that the optical axis thereof is inclined in relation to the center line of the light paths. As described in the first modified example, by modifying the traveling direction of the light in this manner, the angle obtained by adding the angle of incidence $\theta_0$ to the angle of specular reflection $\theta_1$ may be set narrowly regardless of where the light-emitting element and first light-receiving element are disposed. As a result, an effect of increasing the disposal freedom of the light-emitting element and first light-receiving element is obtained.

Further, in the P sensor 330 of the third modified example, the one-sided convex lens 336 serving as a light condensing member is disposed on at least one of the incident light path and specular reflection light path such that the optical axis thereof aligns with the center line of the light path. As described in the third modified example, by means of this constitution, the angle obtained by adding the angle of incidence $\theta_0$ to the angle of specular reflection $\theta_1$ may be set narrowly without causing a decrease in sensitivity even when the light-emitting element 31 and first light-receiving element 32 are disposed at a remove from the photosensitive drum surface.

Further, the P sensor 330 of the third modified example is provided with the one-sided concave lens 336b, which serves as a light diffusing member, on the specular reflection light path. By providing this one-sided concave lens 336b on the specular reflection light path, the occurrence of "shading" of the specular reflection light caused by irregularities in the attachment angle of the lens can be suppressed. As a result, an effect of increasing the freedom of the attachment angle of the lens is obtained.

Also in the P sensor 330 of the third modified example, the one-sided convex lens 336a is provided on the incident light path such that when the distance from the light-emitting element 31 to the one-sided convex lens 336a is set as $a_1$, the distance from the one-sided convex lens 336a to the photosensitive drum surface is set as $b_1$, the focal distance of the one-sided convex lens 336a is set as $f_1$, the distance from the one-sided concave lens 336b to the first light-receiving element 32 is set as $a_2$, the distance from the photosensitive drum surface to the one-sided concave lens 336b is set as $b_2$, and the focal distance of the one-sided concave lens 336b is set as $f_2$, the one-sided convex lens 336a and one-sided concave lens 336b are disposed so as to satisfy at least one of the two expressions shown in (1). As a result, as described in the third modified example, the transmission efficiency of the specular reflection light to the first light-receiving element 32 can be increased.

Further, in the P sensors 430, 530, 630 of the fourth through sixth modified examples, at least one of the light-emitting element 431, 531 and the first light-receiving element 432, 532 is constituted by surface mounted optical means which are surface mounted on the printed board 34. By constituting the light-emitting element and first light-receiving element as SMDs in this manner, the gap between the elements can be narrowed. Accordingly, the angle obtained by adding the angle of incidence $\theta_0$ to the angle of specular reflection $\theta_1$ may be set narrowly.

Further, by providing the one-sided convex lens 336a, condensing lenses 636, 637, and Fresnel lens 837 serving as light condensing members on at least one of the incident light path, specular reflection light path, and diffuse reflection light path as in the P sensors 330, 630, 830, 930 of the third, sixth, eighth, and ninth modified examples, the effect described in the third modified example, in which the angle obtained by adding the angle of incidence $\theta_0$ to the angle of specular reflection $\theta_1$ may be set narrowly without causing a decrease in sensitivity, the effect described in the first modified example, in which the disposal freedom of the light-emitting element and first light-receiving element is increased, the effect described in the eighth modified example, in which a sufficient amount of diffuse reflection light can be securely received by the second light-receiving element 433, and so on can be obtained.

Further, by providing the condensing lenses 636, 637 serving as light condensing members on both of the incident light path and specular reflection light path as in the P sensor 630 of the sixth modified example, both the light-emitting element 531 and the first light-receiving element 32 can be removed from the photosensitive drum surface without causing a decrease in sensitivity, and hence the disposal freedom of the light-emitting element and first light-receiving element is increased.

Also in the P sensor 630 of the sixth modified example, when the distance from the start point of the incident light path, or in other words the light-emitting element 531, to the condensing lens 636, and the distance from the start point of the specular reflection light path, or in other words the photosensitive drum surface, to the condensing lens 637 are set as a, the distance from the condensing lens 636 to the end point of the incident light path, or in other words the photosensitive drum surface and the distance from the condensing lens 637 to the end point of the specular reflection light path, or in other words the first light-receiving element 32, are set as b, and the focal distance of the condensing lenses is set as f, then the condensing lenses are disposed so as to satisfy the expression shown in (2). As a result, the transmission efficiency of the incident light from the light-emitting element to the illumination target on the photosensitive drum surface and the transmission efficiency of the specular reflection light from the photosensitive drum surface to the first light-receiving element 32 can be raised respectively.

Further, when the surface on the side of the one-sided convex lens 336a and condensing lenses 636, 637 serving as light condensing members or the one-sided concave lens 336b serving as a light diffusing member which opposes the photosensitive drum surface is made flat as in the P sensors 330, 630 of the third and sixth modified examples, then the lens surface can be cleaned easily when soiled by scattered toner, as described in the third modified example.

Further, the P sensors 30, 130, 230, 330, 430 of the first, second, third, and fourth modified examples are constituted such that the light-emitting element 31, 431 and first light-receiving element 32, 432 are sealed into a single package. As a result, work to connect the P sensor to an electrical circuit such as a printed board is made easy, and thus the manufacturing process can be simplified.

Further, by mounting the light-emitting element 531 and first light-receiving element 32 on opposite surfaces of the same printed board 34 as in the P sensor 630 of the sixth modified example, incident light from the light-emitting element 531 heading directly toward the first light-receiving element 32 can be blocked by the printed board 34. As a result, incident light from the light-emitting element 531 can be prevented from being received directly in the first light-receiving element 32, thus enabling accurate detection.

In the P sensor 430 of the fourth modified example, both the light-emitting element 431 and first light-receiving element 432 are Surface Mount Devices (SMDs) which are surface mounted on the same surface of the printed board 34. Further, the light-shielding wall 435a is provided as light shielding means on the segment linking the light-emitting element 431 and first light-receiving element 432. As a result, incident light from the light-emitting element 431 heading directly toward the first light-receiving element 432 can be blocked by the light-shielding wall 435a, and thus incident light from the light-emitting element 431* can be prevented from being received directly in the first light-receiving element 432*, enabling accurate detection. As described in the fourth modified example, by using a mounted device mounted on the printed board 34 as the light-shielding means, a member which is not an electronic component no longer has to be provided on the substrate, and hence a large circuit space can be secured. Further, as described in the fourth modified example, by providing a through hole in the substrate surface on the segment linking the light-emitting element 431 and first light-receiving element 432, the reflection of incident light emitted from the light-emitting element 431 on the substrate surface such that the incident light is received directly in the first light-receiving element 432 can be suppressed, thus enabling accurate detection.

Further, by providing a constitution in which the mounted devices do not block the light paths as in the P sensors 530, 630 of the fifth and sixth modified examples, a situation in which light is blocked by the mounted devices such that the amount of light received by the first light-receiving element 532 is insufficient can be avoided.

Further, by surface mounting the surface mount devices on the substrate opposing the light path as in the P sensor 630 of the sixth modified example, the light-squeezing effect can be enhanced.

In the P sensors 30, 130, 230, 330, 430, 530, 630, 730, 830, 930 of the first embodiment, including each of the modified examples described above, if the diaphragm diameter of the incident light $L_1$ from the light-emitting element 31, 431, 531 is set to be larger than the diaphragm diameter of the specular reflection light $L_2$ entering the first light-receiving element 32, 432, 532, then the resolution of the line-form reference pattern formed on the photosensitive drum is enhanced, and the toner adhesion amount can be detected in even more detail.

Further, in the P sensors 730, 830, 930 of the seventh through ninth modified examples, the second light-receiving element 33, 433 is disposed outside of the first virtual plane including the incident light path and specular reflection light path. By means of this constitution, the diffuse reflection light receiving distance r can be set sufficiently short and the diffuse reflection light receiving angle $\theta_2$ can be set sufficiently narrowly without being obstructed by the light-emitting element 31, 431, 531 or the first light-receiving element 32, 432, 532. As a result, the reception efficiency of diffuse reflection light in the second light-receiving element 33, 433 can be raised, and the detection sensitivity of diffuse reflection light can be improved. Further, when the second light-receiving element 33, 433 is disposed such that the diffuse reflection light receiving distance r is set sufficiently short and the diffuse reflection light receiving angle $\theta_2$ is set sufficiently narrowly, this disposal has no effect on the disposal of the light-emitting element 31, 431, 531 and first light-receiving element 32, 432, 532. Hence, as described above, the detection sensitivity of diffuse reflection light can be improved while reducing the distance between the light-emitting element and first light-receiving element such that the shadow factor is reduced and the detection sensitivity of specular reflection light is improved.

Further, by mounting both the light-emitting element 531 and first light-receiving element 532 on the same surface of the printed board 34 and mounting the second light-receiving element 33 on the opposite surface of the printed board 34 as in the P sensor 930 of the ninth modified example, incident light from the light-emitting element 531 heading directly toward the second light-receiving element 33 can be blocked by the printed board 34. Hence incident light from the light-emitting element 531 is not received directly by the second light-receiving element 33, thus enabling accurate detection.

Further, by employing a constitution in which the lead wire of the second light-receiving element 33 is soldered to the printed board 34 as in the P sensor 730, 930 of the seventh and ninth modified examples, then by extending the lead wire as described in the seventh modified example, the second light-receiving element 33 alone can be disposed in the vicinity of the photosensitive drum surface, even when the printed board 34 is disposed at a remove from the photosensitive drum surface. Hence the detection sensitivity of diffuse reflection light can be improved regardless of where the printed board 34 is disposed.

The P sensors 830, 930 of the eighth and ninth modified examples further comprise a casing 835 which surrounds the region of the diffuse reflection light path, along which the diffuse reflection light received by the second light-receiving element 33, 433 travels, that is adjacent to the second light-receiving element. A reflection surface which reflects the diffuse reflection light $L_3$ is provided on the inner wall of the casing 835. A white surface or a mirror surface may be employed as the reflection surface. By means of such a constitution, as described in the eighth modified example, diffuse reflection light entering the interior of the casing 835 can be condensed into the second light-receiving element 33, 433, and hence a sufficient amount of diffuse reflection light can be received securely.

The P sensors 830, 930 of the eighth and ninth modified examples are further provided with a light transmitting member at the inlet opening for the diffuse reflection light $L_3$ to enter the casing 835. A Fresnel lens, for example, may be used as this light transmitting member. As described in the eighth modified example, by providing a light transmitting member at the inlet opening of the casing 835 in this manner, foreign matter such as scattered toner can be prevented from infiltrating the interior of the casing 835, and hence foreign matter can be prevented from becoming transferred to the second light-receiving element 433.

Further, the printer according to the first embodiment, including each of the modified examples described above, comprises the photosensitive drum 5 serving as an image carrier having a surface which specularly reflects light, the charging roll 6 which serves as toner image forming unit for forming a toner image on the photosensitive drum 5, the optical fabrication apparatus 8 and developing apparatus 10, the P sensor which serves as an optical sensor for detecting a toner adhesion amount when toner is transferred to the photosensitive drum 5 by the toner image forming unit, and the control portion serving as image density control unit for performing image density control on the basis of the detection results of the P sensor. By using the P sensors 30, 130, 230, 330, 430, 530, 630, 730, 830, 930 described above as the P sensor, appropriate image density control can be performed.

Further, the toner used in the first embodiment is toner with a weight average particle diameter of 8 micrometers or less, and as described above, the toner adhesion amount must be detected with sufficient sensitivity even in regions with a large toner adhesion amount. By using the P sensors 30, 130, 230, 330, 430, 530, 630, 730, 830, 930 described above, however, the toner adhesion amount can be detected with sufficient sensitivity even in regions with a large toner adhesion amount.

The toner used in the first embodiment also has an average roundness of at least 0.93, and as described above, the toner adhesion amount must be detected with sufficient sensitivity even in regions with a large toner adhesion amount. By using the P sensors 30, 130, 230, 330, 430, 530, 630, 730, 830, 930 described above, however, the toner adhesion amount can be detected with sufficient sensitivity even in regions with a large toner adhesion amount.

Note that in the first embodiment, the present invention is described using a P sensor which detects toner adhesion amounts on a photosensitive drum surface as an example. However, similar effects may be obtained when the present invention is applied to other optical sensors. For example, the present invention may also be applied to an optical sensor or the like which detects the amount of toner transferred to a predetermined location for detecting the amount of scattered toner. Moreover, the present invention is not limited to an image formation apparatus, and may be applied similarly to an optical sensor in another field for detecting the adhesion amount, adhesion position, and so on of an object.

Further, the constitutions in the first embodiment relating to the reception of specular reflection light, such as those described in the first through sixth modified examples, may be applied appropriately to the constitutions relating to the reception of diffuse reflection light, and the constitutions relating to the reception of diffuse reflection light, such as those described in the seventh through ninth modified examples, may be applied appropriately to the constitutions relating to the reception of specular reflection light.

In the first embodiment, a tandem-type image formation apparatus comprising the four image-forming units 4Y, 4M, 4C, 4Bk and employing a direct transfer system in which toner images are transferred directly from each photosensitive drum onto recording paper was described, but the present invention is not limited thereto, and may be applied similarly to image formation apparatuses of various types and employing various systems. In other words, the present invention may be applied similarly to a one drum type image formation apparatus having only a single image-forming unit, an indirect transfer system image formation apparatus in which the toner on the photosensitive drum is first transferred onto an intermediate transfer body and then transferred onto recording paper, and so on.

The constitution of a P sensor 1030 of the second embodiment will now be described. The P sensors provided in each of the image-forming units 4Y, 4M, 4C, 4Bk illustrated in FIG. 2 are constituted identically, and hence a P sensor 1030M provided in the magenta image-forming unit 4M will be used as an example in the following description. Note that in the following description, the color differentiating symbols Y, M, C, and Bk have been omitted where appropriate.

Figure 16:
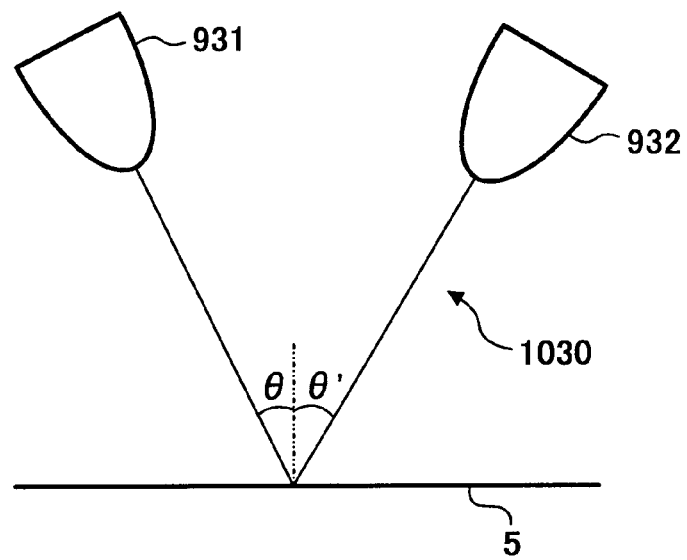
FIG. 16 is a schematic of a typical system of a reflection-type optical sensor according to a second embodiment of the present invention.

First, the general constitution of the reflection type optical sensor optical system used as the P sensor 1030 is shown in FIG. 16. Light emitted from a light-emitting element 931 enters a detection object at an angle of $\theta_1$ to the perpendicular of a reflection surface 5. Light that is reflected at an angle of $\theta_2$ to the perpendicular of the reflection surface 5 from among the light that enters and is reflected by the reflection surface 5 is detected by a light-receiving element 932. When the optical sensor is a system for detecting specular reflection light, then $\theta_1 = \theta_2$, and if the optical sensor is a system for detecting diffuse reflection light, then $\theta_1$ and $\theta_2$ are set to arbitrary values.

Design of the optical system comprising the light-emitting element and light-receiving element, including the values of $\theta_1$ and $\theta_2$, and the positional relationship of the light-emitting element and light-receiving element are determined according to detection object conditions such as reflectance and detection conditions such as the attachment position. The design is also optimized in consideration of various other conditions so that reflection light can be detected efficiently. There exist systems with one light-emitting element and one light-receiving element, such as that shown in FIG. 16, and optical systems employing a plurality of light-emitting elements and light-receiving elements, for example one light-emitting element to two light-receiving elements, two light-emitting elements to two light-receiving elements, and so on. In optical systems employing lenses and so on in double roles to improve the light condensing efficiency, the optical system is determined by a more complicated design process. In other words, if irregularities in the individual components constituting the optical system are not suppressed to the greatest extent possible, an optical sensor with a highly precise detection characteristic cannot be realized. In the optical system of a conventional optical sensor, in which a lead type light-emitting element and light-receiving element are inserted into a resin case, the resin case itself determines the optical system. By fitting the light-emitting element and light-receiving element into the resin case, positioning and optical axis alignment of the light-emitting element and light-receiving element are achieved, and since the resin case can be created with a high degree of precision, a system with few irregularities can be realized.

However, it is difficult to mount a surface mounted element by fitting the element into a resin case (to reflow), and positioning of the surface mounted element is determined according to the degree of mounting on the substrate. Moreover, there are limits to the positioning precision when the surface mounted element is mounted on the substrate, and hence precise positioning cannot be performed in comparison with a lead type element which is positioned according to the resin case. In the second embodiment, in order to absorb irregularities in the positioning precision of a mounted device which causes deterioration in the positioning precision, a constitution is employed in which a sensor using surface mounted elements is provided with a diaphragm.

The diaphragm is an opening which narrows the amount of light (luminous flux) emitted from the light-emitting element or the amount of light (luminous flux) received by the light-receiving element. The luminous flux which passes through the diaphragm from among the light emitted by the light-emitting element becomes an effective emitted light amount, and the luminous flux which passes through the diaphragm to be received by the light-receiving element becomes an effective received light amount.

In an optical system which does not use a diaphragm, all of the light that is emitted from the light-emitting element toward the reflection surface contributes to the detection characteristic. Hence, if the position of the light-emitting element deviates from a predetermined position, the amount of light impinging upon the reflection surface fluctuates, deviations occur in the optical axis of the system, and as a result, irregularities arise in the detection characteristic.

Figure 17A:
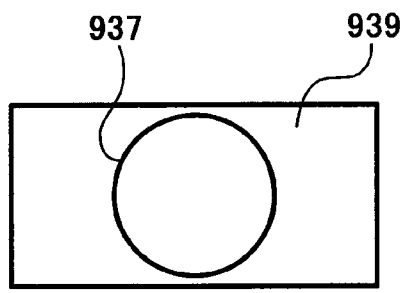
FIG. 17A and FIG. 17B are schematics for illustrating an example of a surface mounted element.
Figure 17B:
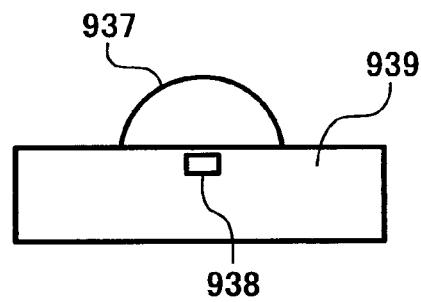

FIG. 17A and FIG. 17B are schematics for illustrating an example of a surface mounted element. The surface mounted element is constituted such that a light emitting body (or light receiving body) 938 is attached to a main body portion 939, and the light emitting body (or light receiving body) is covered by a lens portion 937. In the case of a surface mounted light-emitting element, light emitted from the light emitting body 938 is generated to the outside uniformly through the lens portion 937. In the case of a surface mounted light-receiving element, reflection light that is emitted from the light-emitting element and reflected by the detection object is received through the lens portion 937, whereupon the reflection light is detected by the light receiving body 938.

Figure 18A:
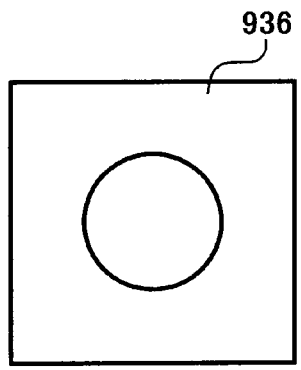
FIG. 18A to FIG. 18D are schematics for illustrating a positional relationship between a diaphragm and a lens of the surface mounted element.

FIG. 18A to FIG. 18D are schematics for illustrating a positional relationship between the lens portion 937 of a surface mounted element and a diaphragm 936. In the case of a light-emitting element, it is important to ensure that the amount of light impinging on the reflection surface from the light-emitting element is maintained at a constant level without fluctuations, and hence the use of a diaphragm may be considered. A case in which the diaphragm 936 shown in FIG. 18A is disposed in front of a surface mounted light-emitting element having a spherical lens such as that of FIG. 17A and FIG. 17B will be considered. Note that a diaphragm having a circular form is employed, but the diaphragm may take another form.

Figure 18B:
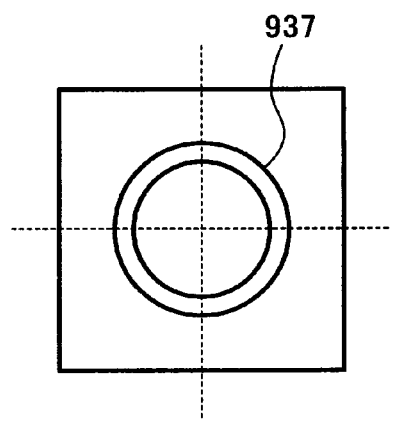

FIG. 18B shows a state in which the optical axis of the light-emitting element (in most cases, the central axis of the lens) and the center of the diaphragm align. In this state, light is emitted from the entire cross section of the diaphragm, and hence a desired amount of light can be extracted from the light-emitting element in accordance with the diameter of the diaphragm.

Figure 18C:
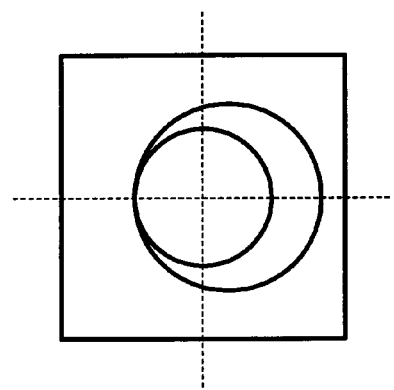

FIG. 18C shows a case in which the light-emitting element deviates to the right side of the diaphragm. In the state shown in FIG. 18C, similarly to that shown in FIG. 18B, light is emitted from the entire cross section of the diaphragm, and hence a desired amount of light can be extracted from the light-emitting element in accordance with the diameter of the diaphragm.

Figure 18D:
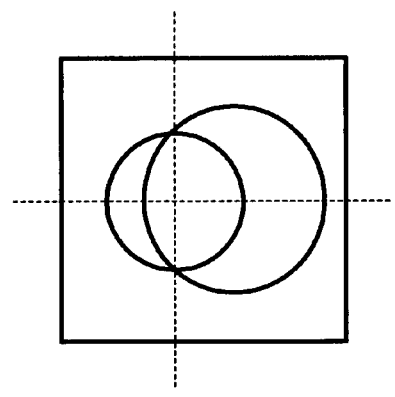

However, if the light-emitting element deviates further to the right side, the cross section from which light is emitted becomes smaller than the cross section of the diaphragm, as shown in FIG. 18D, leading to the occurrence of so-called "shading", and hence a desired amount of light cannot be obtained. By setting the diameter of the diaphragm to be smaller than the diameter of the lens of the light-emitting element, a predetermined amount of light passing through the diaphragm can be maintained at a constant level even when the element deviates between the states of FIG. 18B and FIG. 18C.

Similar can be the of a light-receiving element. Light emitted from the light-emitting element is specularly reflected or diffused on the reflection surface, whereupon a predetermined amount of reflection light passes through the diaphragm in front of the light-receiving element. If the positions of the diaphragm and light-receiving element are aligned accurately, then a predetermined amount of light is received in the light-receiving element without problems, as shown in FIG. 18A. Even if the position of the light-receiving element deviates, as long as the deviation is within the range of FIG. 18B to FIG. 18C, the amount of light passing through the diaphragm can be received in the light-receiving element in its entirety. By providing the diaphragm in this manner, positional deviation can be permitted within a wide range in which shading does not occur.

As described above, positional deviation of the light-emitting element or light-receiving element can be absorbed by a diaphragm. In other words, irregularities in the precision of mounting position determination occurring when a device is mounted onto a substrate can be absorbed as long as the positional relationship between the surface mounted element and diaphragm is within the range between FIG. 18B and FIG. 18C in which shading caused by device mounting irregularities does not occur.

A process in which irregularities in the mounting positioning precision are ±d will be considered. It is assumed that the lens diameter of the mounted element is Rd, and the diaphragm diameter is Rs. The relationship of Rd and Rs for satisfying FIG. 18B is Rd>Rs. If the shading margin in FIG. 18C is set as the maximum mounting irregularity value, then shading does not occur. Rs is also set to satisfy Rs<Rd−2d in consideration of the fact that positional deviation may also occur in the opposite direction. In so doing, light emitted from the light-emitting element passes through the diaphragm without shading even when irregularity is at its maximum value, and the amount of reflection light that passes through the diaphragm is able to enter the light-receiving element without shading. As a result, irregularities in the optical characteristic of the sensor due to mounting irregularities can be reduced.

As a result of research performed by the present inventors, it was ascertained that when an optical sensor is constructed using a surface mounted light-emitting element with a lens diameter of 2 mm, mounting can be performed with a precision of ±0.2 mm of production line mounting irregularity. Hence if the diameter of the diaphragm in the light-emitting element is designed to be smaller than 2−2*0.2 mm, or in other words no more than 1.6 mm, mounting irregularities can be absorbed by the diaphragm. In light of further evaluations as to whether the amount of light from the light-emitting element is appropriate and so on, the diameter of the diaphragm in the light-emitting element was set at 1.2 mm.

Further, a surface mounted light-receiving element in which both the light-receiving element and the lens diameter are 2 mm was selected, and hence mounting irregularities can be absorbed by designing the diaphragm of the light-receiving element to be no more than 1.6 mm. To achieve an improvement in light receiving efficiency, the diaphragm of the light-receiving element was set at 1.4 mm, which is wider than that of the light-emitting element.

When attempting to obtain an even more precise detection characteristic, the manner in which characteristics unique to the elements affect the detection characteristic can be considered. Various types of light-emitting element and light-receiving element exist, such as those with wide directivity, narrow directivity, sensitivity distribution, and so on. When a light-emitting element with extremely narrow directivity, for example, is used such that the optical output at the center of the element is as strong as possible, in an optical system using a diaphragm variation in the amount of light passing through the diaphragm can be a cause of irregularities even when shading does not occur. It is therefore preferable to combine an element in which the optical intensity in the traveling direction of the light is uniform as the light-emitting element, and an element in which the light receiving sensitivity is uniform as the light-receiving element. When such a combination is used, the amount of light emitted from the light-emitting element to pass through the diaphragm can be maintained at a constant level even when mounting irregularities occur, and a uniform light receiving characteristic can be obtained regardless of the part of the light-receiving element in which light is received. Thus an optical sensor with even higher precision can be realized.

Figure 19:
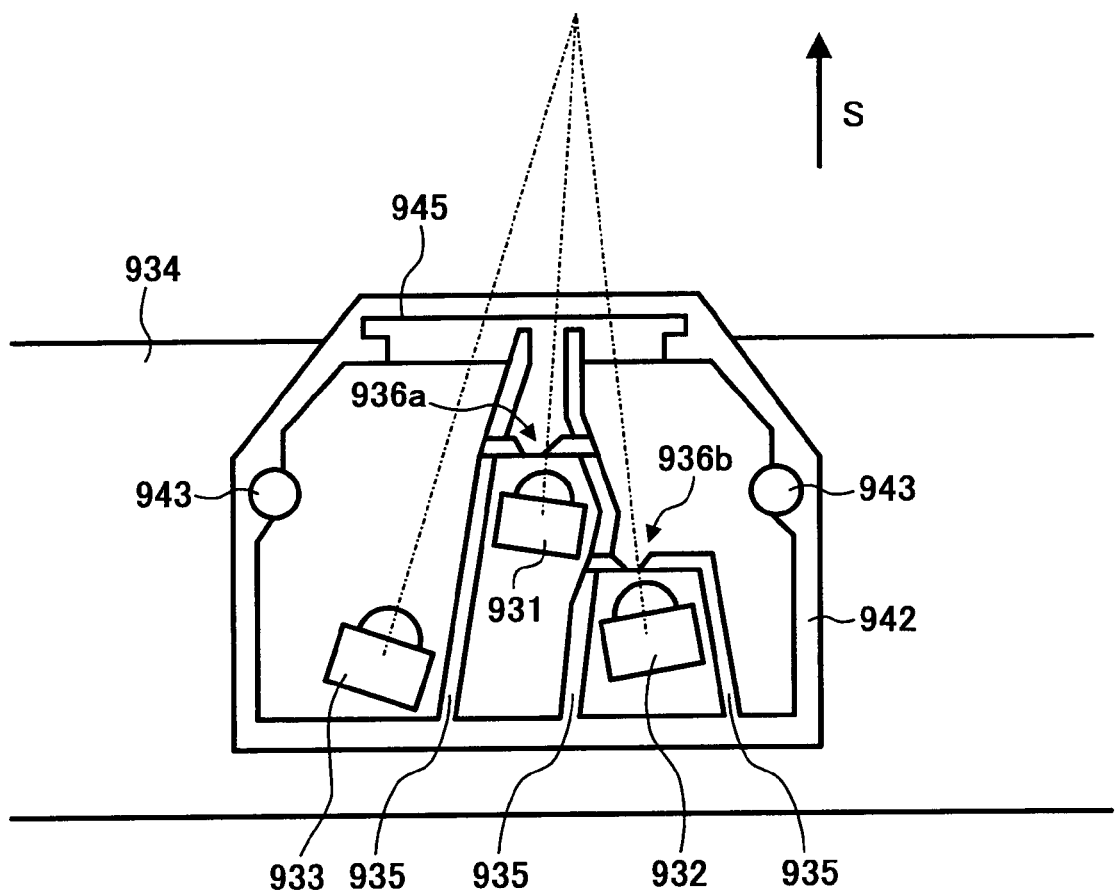
FIG. 19 is a schematic of an example of the optical sensor.

FIG. 19 is a schematic of an example of the optical sensor 1030. FIG. 19 is a perspective view seen from the upper portion of the sensor of a state in which the surface mounted light-emitting element 931, the first light-receiving element 932 for receiving specular reflection light, and a second light-receiving element 933 for receiving divergent reflection light are mounted on a substrate 934 and covered from above with a resin case 942. A resin material which does not transmit light (LED light or disturbance light) is preferable as the resin material of the resin case 942, and hence a black polycarbonate or the like is used. An arrow S indicates the detection direction of the P sensor 1030.

Position alignment of the respective diaphragms 936a, 936b of the surface mounted light-emitting element 931 and first light-receiving element 932 that are mounted on the substrate 934 is realized by fitting the resin case 942 which has been subjected to diaphragm processing so as to block disturbance light onto the substrate 934. As well as the diaphragms 936a, 936b, the resin case 942 is provided with a light-shielding wall 935 with the function of blocking light in the interior of the case (preventing cross-talk), and a projection 943 for engaging with the substrate 934. Position alignment between the substrate, or in other words the surface mounted elements, and the resin case is performed by fitting the projection 943 into a positioning hole in the substrate 934. Since the diaphragms 936a, 936b are also provided in the resin case 942, positioning of the surface mounted elements and diaphragms can be performed easily using this method. In the case of an optical system using a lens 945 as in the drawing, the lens 945, diaphragms 936a, 936b, and resin case 942 can be integrated by applying processing of the lens 945 or positioning processing of the lens 945 to the resin case 942. In so doing, positioning of the surface mounted elements can be realized through positioning of the substrate and case.

Figure 20A:
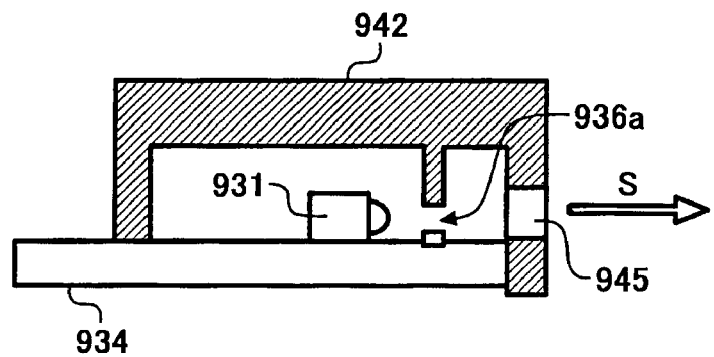
FIG. 20A and FIG. 20B are cross sections of the optical sensor and a mounting substrate.
Figure 20B:
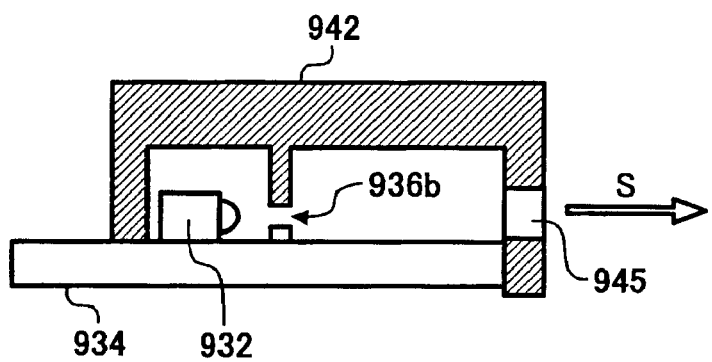

FIG. 20A and FIG. 20B are cross sections of the substrate 934 and P sensor 1030. FIG. 20A is a sectional view of the P sensor 1030 in the vicinity of the light-emitting element 931. It can be seen that the diaphragm 936a is constituted with a smaller diameter than the light-emitting element 931, and hence the amount of light emitted from the light-emitting element 931 in the detection direction S is restricted.

FIG. 20B is a sectional view of the P sensor 1030 in the vicinity of the first light-receiving element 932. It can be seen that the diaphragm 936b is constituted with a smaller diameter than the first light-receiving element 932, and hence the amount of reflection light which enters the first light-receiving element 932 from the detection direction S is restricted.

Figure 21A:
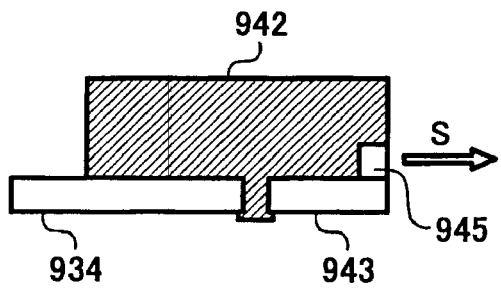
FIG. 21A and FIG. 21B are schematics for illustrating a method of fixing a case to the mounting substrate.
Figure 21B:
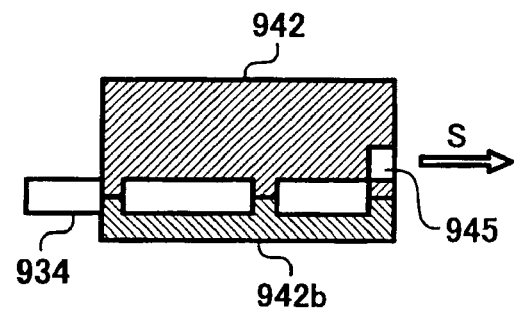
Figure 24:
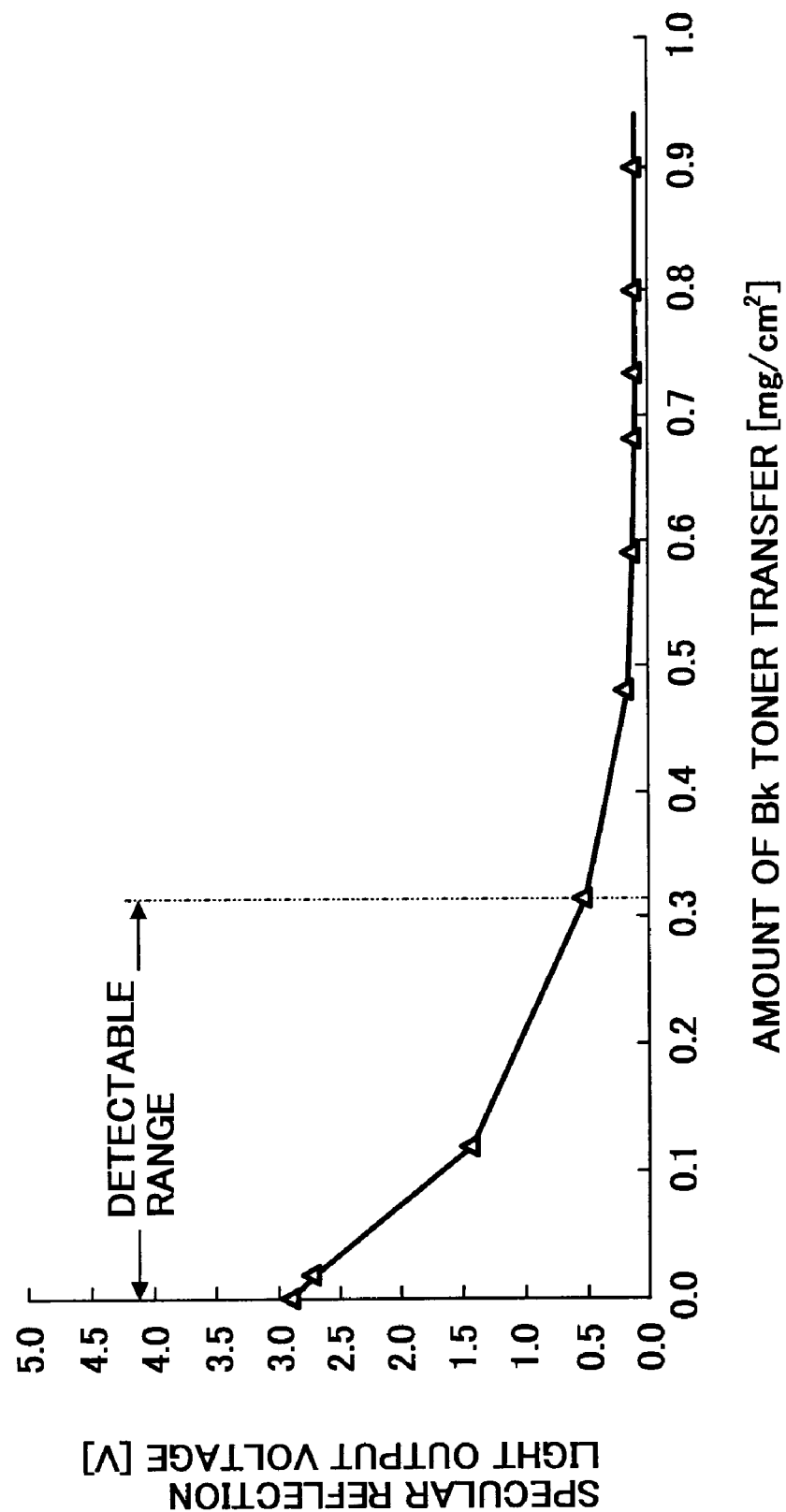
FIG. 24 is a graph for illustrating a relationship between an amount of black toner transferred to the surface of the photosensitive drum and the output voltage of the P sensor that detects specular reflection light.
Figure 25:
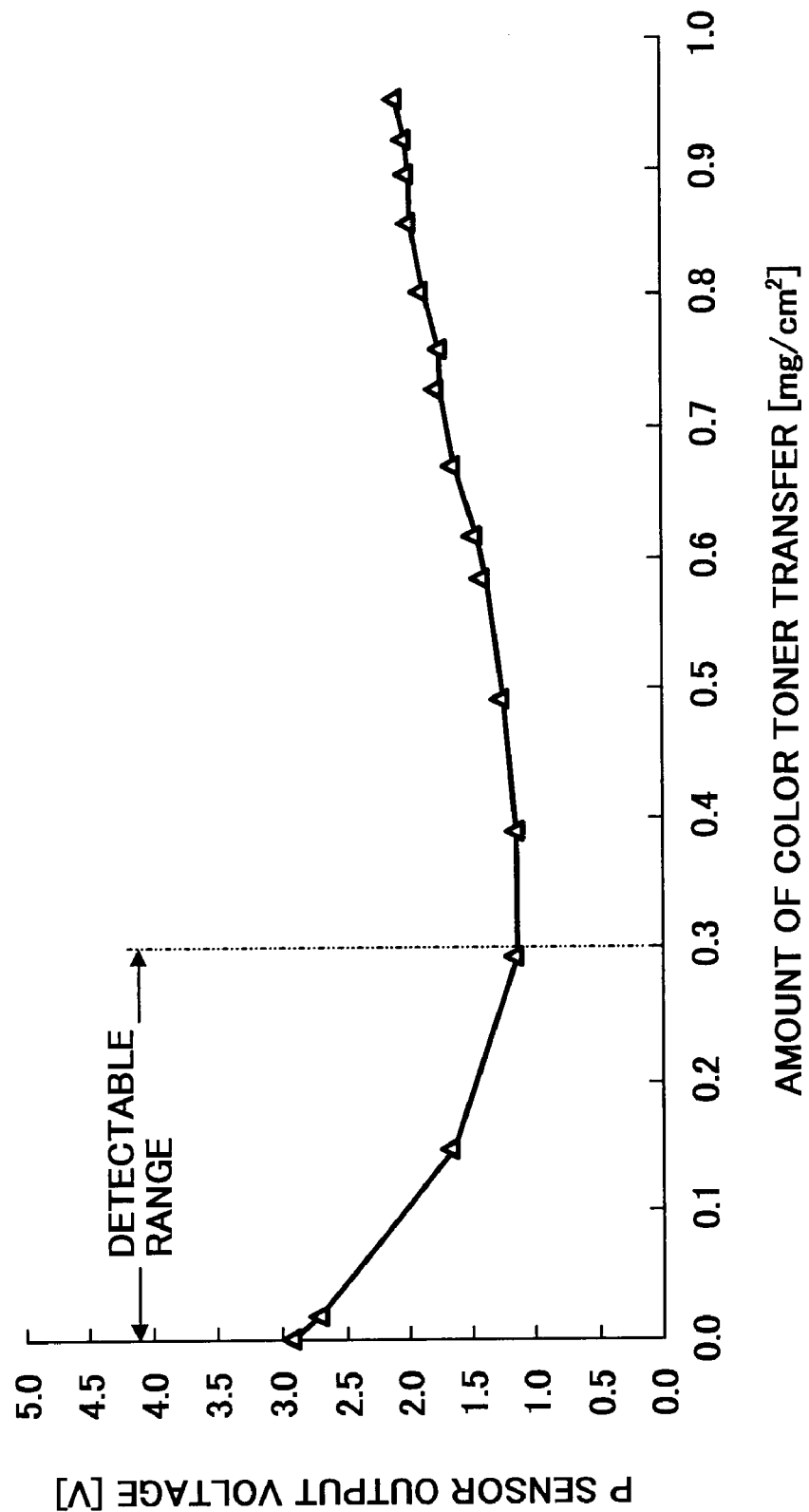
FIG. 25 is a graph for illustrating a relationship between an amount of color toner transferred to the surface of the photosensitive drum and the output voltage of the P sensor that detects specular reflection light.
Figure 26:
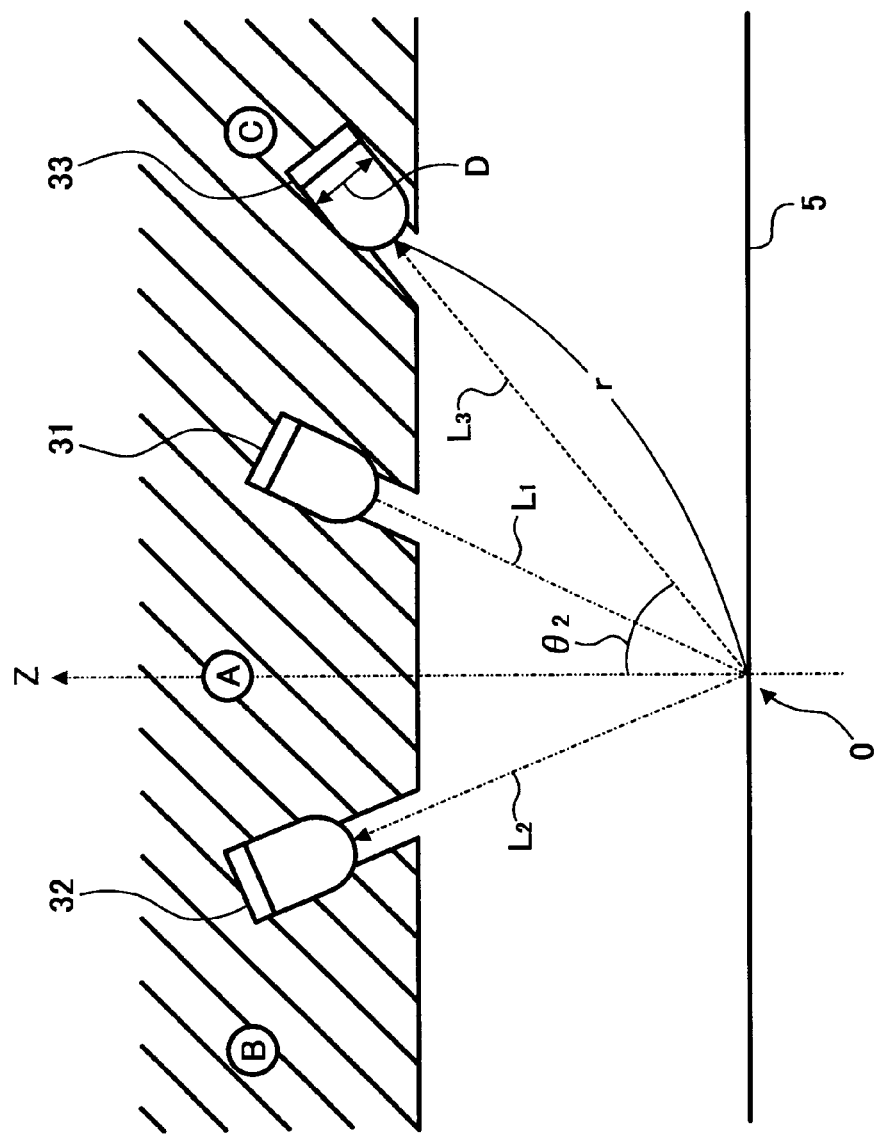
FIG. 26 is a schematic for illustrating a layout of a light-emitting element, a first light-receiving element that receives specular reflection light, and a second light-receiving element that receives diffuse reflection light in a conventional optical sensor.

FIG. 21A and FIG. 21B are schematics for illustrating a method for fixing the resin case 942 and substrate 934. FIG. 21A illustrates a fixing method using thermal welding. In this method, the fitting projection 943 on the resin case 942 is fitted into the positioning hole in the substrate 934, and the projection 943 is subjected to thermal welding on the opposite side of the substrate 934 to the P sensor, whereby the resin case 942 and substrate 934 are fixed together completely. FIG. 21B illustrates a fixing method in which the substrate 934 is held between two resin cases 942. In this method, the projection 943 of a resin case 942(a) on the upper face side of the substrate 934 and a projection of a resin case 942(b) on the lower face side of the substrate are passed through the positioning hole of the substrate 934 such that the two cases are meshed together, and thus the resin case 942 is fixed to the substrate 934.

FIG. 22 is a schematic for illustrating an example of assembly of the optical sensor 1030. Three P sensors 1030 are used to perform reading of toner patterns on a photosensitive body or transfer belt and detection of the toner adhesion amount, color deviation, and so on. Once the surface mounted light-emitting element and light-receiving element have been mounted together with an optical sensor driving circuit, the case is placed over. When surface mounted elements are used as the light-emitting element and light-receiving element, the optical sensor can be reduced in size in comparison with cases in which lead type devices are used. Moreover, the number of manual processing steps decreases, leading to cost reductions and improvements in productivity.

The image formation apparatus using an optical sensor according to the second embodiment described above comprises at least one light-emitting element 931 serving as light emitting unit, and the light-receiving elements 932, 933 serving as light receiving unit for receiving reflection light generated when incident light emitted from the light-emitting element 931 is reflected by the photosensitive drum 5 which is the illumination object. This image formation apparatus is constituted such that at least one of the light-emitting element 931 and light-receiving element 932 is surface mounted onto the printed board 934, and comprises on the light path between the surface mounted elements and photosensitive drum a diaphragm 936 serving as a light-transmitting hole which is smaller than the surface area of the light path.

According to this constitution, by providing the diaphragm 936, in which no positioning precision irregularities occur, on the light path in the illumination direction of the light-emitting element 931, the orientation of the light and amount of light with which the detection object is irradiated can be held at a constant level even when irregularities occur within a predetermined range in the mounting position of the light-emitting element 931 on the substrate 934 and in the light path.

Further, by providing the diaphragm 936, in which no positioning precision irregularities occur, on the light path of the reflection light that enters the light-receiving element 932, a constant detection result can be obtained for the reflected waves from the detection subject even when irregularities occur within a predetermined range in the mounting position of the light-receiving element 932 on the substrate 934. Also in the second embodiment, by means of a constitution in which Rs and Rd satisfy a relationship of Rs<Rd−2d, where Rs is the diametrical length of the diaphragm 936, Rd is the diametrical length of a cross section of the light path before passing through the diaphragm 936, and the margin of error in positioning precision when performing surface mounting onto the circuit is ±d, irregularities in positioning precision during surface mounting can be absorbed even more reliably.

Also in the second embodiment, the optical intensity of the light-emitting element 931 is uniform over the light emitting surface thereof. By means of such a constitution, the detection object can be irradiated with illumination light having even fewer irregularities.

Also in the second embodiment, the optical sensitivity of the light-receiving elements 932, 933 is uniform over the light receiving surfaces thereof. By means of such a constitution, irregularities in the detection results for the same reflection light can be reduced even further.

Further, in the second embodiment the light-emitting element 931 and light-receiving elements 932, 933 are accommodated in a light-shielding resin case 942, and processing of the diaphragm 936 is applied to the resin case 942. By means of such a constitution, an optical sensor which is capable of high-precision detection can be created easily.

Further, in the second embodiment the positioning projection portion 943 is provided on the resin case 942, and the positioning hole portion is provided in the printed board 934 on which the light-emitting element 931 and light-receiving elements 932, 933 are mounted. By fitting the projection portion 943 into the hole portion, the resin case 942 can be fixed onto the printed board. By means of such a constitution, positioning of the sensor can be performed with a high degree of precision simply by providing a projection portion on the resin case.

Further, in the second embodiment the tip end of the projection portion 943 on the resin case 942 is thermally welded to the printed board 934. By means of such a constitution, the sensor, which has been positioned with a high degree of precision, can be fixed to the printed board.

Also in the second embodiment, the resin case 942 is provided with a two-component constitution. By disposing one of the resin cases 942a from above the printed board, and disposing the other resin case 942b from below the printed board 934, the printed board 934 is held between the resin case 942, and by meshing the resin case 942a on the printed board 934 and the resin case 942b below the printed board 934 together, the resin case 942 is fixed to the printed board 934. By means of such a constitution, the sensor, which has been positioned with a high degree of precision, can be fixed to the printed board.

According to the present invention, a meritorious effect is obtained whereby the range in which an adhesion amount of an object that does not specularly reflect light existing on an illumination object that does specularly reflect light can be detected with good sensitivity is expanded in comparison with the prior art.

Furthermore, according to the present invention, the optical sensor can be used, for example, to detect the adhesion amount of an object which absorbs light or reflects light diffusely when the object adheres to the illumination object, to detect the adhesion position of such an object, and so on from the detection result of at least one of the specular reflection light and diffuse reflection light.

Moreover, according to the present invention, the surface area of the part of the illumination object that does not contribute to the specular reflection light that is received by the first light receiving unit can be brought sufficiently close to the surface area of the part of the illumination object that is actually occupied by the object transferred to the illumination object. In other words, the shadow factor can be reduced. Hence, even large adhesion amounts of the object can be detected with sufficient sensitivity, and the range in which the adhesion amount can be detected with good sensitivity expands.

Furthermore, according to the present invention, the angle formed by the center line of the incident light path directly before the illumination object and the center line of the specular reflection light path directly after reflection on the illumination object can be narrowed without losing sensitivity.

Moreover, according to the present invention, there is no need to remove the light emitting unit and first light receiving unit from the illumination object, and hence the sensitivity of the optical sensor does not decrease.

Furthermore, according to the present invention, it is still possible to narrow the gap between surface mounted optical elements even further, and thus to narrow the aforementioned angle sufficiently.

Moreover, according to the present invention, the angle formed by the surface normal direction at the reflection point O of the illumination object 5 and the center line of the diffuse reflection light path $L_3$ of the diffuse reflection light that is received by the second light-receiving element 33 can be narrowed. Thus, the light receiving efficiency of diffuse reflection light can be improved in comparison with that of the prior art, and the amount of diffuse reflection light received by the second light receiving unit can be increased.

Furthermore, according to the present invention, even if the amount of the toner is large, it is possible to detect the toner with a high sensitivity.

Moreover, according to the present invention, a fixed amount of reflection light in a fixed orientation can be obtained from the illumination object, and thus irregularities in the light receiving sensitivity of the light receiving unit can be suppressed.

Furthermore, according to the present invention, irregularities in the light receiving sensitivity of the light receiving unit can be suppressed.

Moreover, according to the present invention, irregularities in the light receiving sensitivity can be suppressed even when a certain amount of error occurs during surface mounting, and hence any irregularities in the detection characteristic of a sensor that can occur among the various components of an optical sensor can be suppressed.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. An optical sensor comprising:
   at least one light emitting unit that emits a light on an incident light path toward an illumination object;
   a first light receiving unit that receives specular reflection light on a specular reflecting light path at an angle of specular reflection from the illumination object when the light is incident on the illumination object;

a light condensing member provided on the incident light path; and a light diffusing member provided on the specular reflection light path;

wherein a sum of the incident angle and the angle of specular reflection is 25 degrees or less; and $$1/a1 + 1/(b1+b2) = 1/f1 \text{ or}$$

$$1/a2 + 1/(b1+b2) = 1/f2 \quad (1)$$

in which a1 is a distance from the light emitting unit to the light condensing member, b1 is a distance from the light condensing member to the illumination object, a2 is a distance from the light diffusing member to the first light receiving element, b2 is a distance from the illumination object to the light diffusing member, f1 is a focal distance of the light condensing member, and f2 is focal distance of the light diffusing member.

2. The optical sensor according to claim 1, wherein the sum of the incidence angle and the reflection angle is 20 degrees or less.

3. The optical sensor according to claim 1, wherein at least one of the at least one light emitting unit and the first light receiving unit includes an optical element surface mounted on a substrate.

4. The optical sensor according to claim 1, wherein the at least one light emitting unit and the first light receiving unit are mounted on a same printed board and sealed in a single package.

5. The optical sensor according to claim 1, wherein a spot size of the light from the at least one light emitting unit is larger than a spot size of the specular reflection light entering the first light receiving unit.

6. The optical sensor according to claim 1, further comprising a second light receiving unit disposed outside of a virtual plane including incident light path along which the light from the light emitting unit travels to the illumination object and the specular reflection light path along which the specular reflection light travels to the first light receiving unit.

7. An image forming apparatus, comprising:

an optical sensor comprising:

at least one light emitting unit that emits a light on an incident light path toward an illumination object;

a first light receiving unit that receives specular reflection light on a specular reflecting light path at an angle of specular reflection from the illumination object when the light is incident on the illumination object;

a light condensing member provided on the incident light path; and a light diffusing member provided on the specular reflection light path;

wherein a sum of the incident angle and the angle of specular reflection is 25 degrees or less; and $$1/a1 + 1/(b1+b2) = 1/f1 \text{ or}$$

$$1/a2 + 1/(b1+b2) = 1/f2 \quad (1)$$

in which a1 is a distance from the light emitting unit to the light condensing member, b1 is a distance from the light condensing member to the illumination object, a2 is a distance from the light diffusing member to the first light receiving element, b2 is a distance from the illumination object to the light diffusing member, f1 is a focal distance of the light condensing member, and f2 is focal distance of the light diffusing member.

\* \* \* \* \*